United States Patent
Blair et al.

(10) Patent No.: US 9,514,341 B2
(45) Date of Patent: Dec. 6, 2016

(54) METHOD, APPARATUS AND ARTICLE FOR DETECTION OF TRANSPONDER TAGGED OBJECTS, FOR EXAMPLE DURING SURGERY

(71) Applicant: RF Surgical Systems, Inc., Carlsbad, CA (US)

(72) Inventors: William A. Blair, Carlsbad, CA (US); David A. Poirier, Escondido, CA (US); Curtis Crump, Vista, CA (US)

(73) Assignee: Covidien LP, Mansfield, MA (US)

( * ) Notice: Subject to any disclaimer, the term of this patent is extended or adjusted under 35 U.S.C. 154(b) by 116 days.

(21) Appl. No.: 14/327,208

(22) Filed: Jul. 9, 2014

(65) Prior Publication Data
US 2015/0272688 A1 Oct. 1, 2015

Related U.S. Application Data

(60) Provisional application No. 61/972,832, filed on Mar. 31, 2014.

(51) Int. Cl.
*H04Q 5/22* (2006.01)
*G06K 7/10* (2006.01)
(Continued)

(52) U.S. Cl.
CPC .......... *G06K 7/10386* (2013.01); *A61B 5/061* (2013.01); *A61B 90/90* (2016.02); *A61B 90/98* (2016.02); *G01V 15/00* (2013.01); *A61B 2505/05* (2013.01)

(58) Field of Classification Search
CPC .. A61B 19/44; A61B 5/06; A61B 2019/448; G01V 15/00; G06K 7/10039; G06K 7/10386; G06K 7/10336

USPC ............................................... 340/10.1–10.6
See application file for complete search history.

(56) References Cited

U.S. PATENT DOCUMENTS

| | | | |
|---|---|---|---|
| 3,422,816 A | 1/1969 | Robinson et al. | |
| 3,587,583 A | 6/1971 | Greenberg | |

(Continued)

FOREIGN PATENT DOCUMENTS

| | | |
|---|---|---|
| AU | 199852698 B2 | 3/1993 |
| AU | 2003249257 A1 | 2/2004 |

(Continued)

OTHER PUBLICATIONS

Blair et al., "Tag and Detection Device," U.S. Appl. No. 60/458,222, filed Mar. 27, 2003, 23 pages.

(Continued)

*Primary Examiner* — Hai Phan
*Assistant Examiner* — Royit Yu

(57) ABSTRACT

The presence or absence of objects is determined by interrogating or exciting transponders coupled to the objects using pulsed wide band frequency signals. Interrogation is broken down into a number of subsample scan cycles each having interrogation cycles a start time forward in time by a fraction of a period of an expected transponder response signal. Ambient or background noise is evaluated and a threshold adjusted based on the level of noise. Adjustment may be based on multiple noise measurements or samples. Noise detection may be limited, with emphasis placed on interrogation to increase the signal to noise ratio. Matched filtering may be employed. Presence/absence determination may take into account frequency and/or Q value to limit false detections. Appropriate acts may be taken if detected noise is out of defined limits of operation, for example shutting down interrogation and/or providing an appropriate indication.

11 Claims, 14 Drawing Sheets

(51) Int. Cl.
*G01V 15/00* (2006.01)
*A61B 5/06* (2006.01)

(56) References Cited

U.S. PATENT DOCUMENTS

| | | |
|---|---|---|
| D240,166 S | 6/1976 | Cartmell et al. |
| 4,034,297 A | 7/1977 | Giorgi et al. |
| 4,114,601 A | 9/1978 | Abels |
| 4,193,405 A | 3/1980 | Abels |
| 4,422,548 A | 12/1983 | Cheesman et al. |
| D272,943 S | 3/1984 | Stone et al. |
| 4,540,398 A | 9/1985 | Barson et al. |
| 4,658,818 A | 4/1987 | Miller, Jr. et al. |
| 4,681,111 A | 7/1987 | Silvian |
| 4,893,118 A | 1/1990 | Lewiner et al. |
| 4,966,595 A | 10/1990 | Meringola |
| 4,992,675 A | 2/1991 | Conner, Jr. et al. |
| 5,031,642 A | 7/1991 | Nosek |
| 5,057,095 A | 10/1991 | Fabian |
| 5,105,829 A | 4/1992 | Fabian et al. |
| 5,107,862 A | 4/1992 | Fabian et al. |
| 5,181,021 A | 1/1993 | Lee et al. |
| 5,188,126 A | 2/1993 | Fabian et al. |
| 5,190,059 A | 3/1993 | Fabian et al. |
| 5,231,273 A | 7/1993 | Caswell et al. |
| 5,235,326 A | 8/1993 | Beigel et al. |
| 5,258,742 A | 11/1993 | Soldevila Domingo et al. |
| 5,281,941 A | 1/1994 | Bernstein |
| 5,329,944 A | 7/1994 | Fabian et al. |
| 5,353,011 A | 10/1994 | Wheeler et al. |
| D353,343 S | 12/1994 | Eberhardt |
| 5,390,360 A * | 2/1995 | Scop .............. H04W 28/18 340/10.2 |
| 5,446,447 A | 8/1995 | Carney et al. |
| 5,450,622 A | 9/1995 | Vandegraaf |
| 5,456,718 A | 10/1995 | Szymaitis |
| 5,482,036 A | 1/1996 | Diab et al. |
| D378,614 S | 3/1997 | Jensen |
| 5,629,498 A | 5/1997 | Pollock et al. |
| 5,650,596 A | 7/1997 | Morris et al. |
| 5,664,582 A | 9/1997 | Szymaitis |
| D385,037 S | 10/1997 | Jensen |
| 5,767,816 A | 6/1998 | Cosman |
| 5,923,001 A | 7/1999 | Morris et al. |
| 5,928,151 A | 7/1999 | Hossack et al. |
| 5,931,824 A | 8/1999 | Stewart et al. |
| 5,963,132 A | 10/1999 | Yoakum |
| 6,026,818 A | 2/2000 | Blair et al. |
| D423,673 S | 4/2000 | Bassøe |
| 6,075,797 A | 6/2000 | Thomas |
| 6,093,869 A | 7/2000 | Roe et al. |
| D429,337 S | 8/2000 | Sanfilippo |
| 6,172,608 B1 | 1/2001 | Cole |
| 6,201,469 B1 | 3/2001 | Balch et al. |
| 6,211,666 B1 | 4/2001 | Acker |
| 6,215,437 B1 | 4/2001 | Schürmann et al. |
| 6,223,137 B1 | 4/2001 | McCay et al. |
| 6,232,878 B1 | 5/2001 | Rubin |
| 6,270,460 B1 | 8/2001 | McCartan et al. |
| 6,317,027 B1 | 11/2001 | Watkins |
| 6,349,234 B2 | 2/2002 | Pauly et al. |
| 6,353,406 B1 | 3/2002 | Lanzl et al. |
| 6,354,493 B1 | 3/2002 | Mon |
| 6,359,562 B2 | 3/2002 | Rubin |
| 6,366,206 B1 | 4/2002 | Ishikawa et al. |
| D456,907 S | 5/2002 | Sanfilippo |
| D457,634 S | 5/2002 | Rouns et al. |
| 6,384,296 B1 | 5/2002 | Roe et al. |
| 6,401,722 B1 | 6/2002 | Krag |
| D471,281 S | 3/2003 | Baura et al. |
| 6,557,752 B1 | 5/2003 | Yacoob |
| 6,566,997 B1 | 5/2003 | Bradin |
| 6,588,661 B2 | 7/2003 | Degrauwe et al. |
| 6,632,216 B2 | 10/2003 | Houzego et al. |
| 6,633,226 B1 | 10/2003 | Nysen |
| 6,641,039 B2 | 11/2003 | Southard |
| 6,648,223 B2 | 11/2003 | Boukhny et al. |
| 6,650,143 B1 | 11/2003 | Peng |
| 6,650,240 B2 | 11/2003 | Lee et al. |
| 6,667,902 B2 | 12/2003 | Peng |
| 6,671,040 B2 | 12/2003 | Fong et al. |
| 6,696,954 B2 | 2/2004 | Chung |
| 6,700,151 B2 | 3/2004 | Peng |
| 6,722,783 B2 | 4/2004 | Jackson, Sr. |
| 6,734,795 B2 | 5/2004 | Price |
| 6,744,378 B1 | 6/2004 | Tyburski |
| 6,753,783 B2 | 6/2004 | Friedman et al. |
| 6,766,960 B2 | 7/2004 | Peng |
| D495,055 S | 8/2004 | Silber |
| 6,774,800 B2 | 8/2004 | Friedman et al. |
| 6,777,623 B2 | 8/2004 | Ballard |
| 6,777,757 B2 | 8/2004 | Peng et al. |
| 6,786,405 B2 | 9/2004 | Wiedenhoefer |
| 6,791,891 B1 | 9/2004 | Peng et al. |
| 6,798,693 B2 | 9/2004 | Peng |
| 6,812,824 B1 | 11/2004 | Goldinger et al. |
| 6,812,842 B2 | 11/2004 | Dimmer |
| 6,822,570 B2 | 11/2004 | Dimmer et al. |
| 6,822,888 B2 | 11/2004 | Peng |
| 6,838,990 B2 | 1/2005 | Dimmer |
| 6,856,540 B2 | 2/2005 | Peng et al. |
| D502,419 S | 3/2005 | Copen |
| 6,861,639 B2 | 3/2005 | Al-Ali |
| 6,861,954 B2 | 3/2005 | Levin |
| 6,879,300 B2 | 4/2005 | Rochelle et al. |
| 6,898,116 B2 | 5/2005 | Peng |
| 6,909,366 B1 | 6/2005 | Marsh et al. |
| 6,940,751 B2 | 9/2005 | Peng et al. |
| D511,004 S | 10/2005 | Masuda |
| 6,956,258 B2 | 10/2005 | Peng |
| D511,384 S | 11/2005 | Masuda |
| 6,972,986 B2 | 12/2005 | Peng et al. |
| 6,977,504 B2 | 12/2005 | Wright et al. |
| 6,992,925 B2 | 1/2006 | Peng |
| 6,998,541 B2 | 2/2006 | Morris et al. |
| 7,001,366 B2 | 2/2006 | Ballard |
| 7,019,650 B2 | 3/2006 | Volpi et al. |
| 7,026,924 B2 | 4/2006 | Degrauwe et al. |
| 7,026,927 B2 | 4/2006 | Wright et al. |
| 7,031,209 B2 | 4/2006 | Wang et al. |
| 7,042,722 B2 | 5/2006 | Suzuki et al. |
| D526,586 S | 8/2006 | McCaghren et al. |
| 7,098,793 B2 | 8/2006 | Chung |
| 7,098,866 B2 | 8/2006 | Desjeux et al. |
| 7,118,029 B2 | 10/2006 | Nycz et al. |
| 7,135,973 B2 | 11/2006 | Kittel et al. |
| 7,135,978 B2 | 11/2006 | Gisselberg et al. |
| 7,142,118 B2 | 11/2006 | Hamilton et al. |
| 7,142,815 B2 | 11/2006 | Desjeux et al. |
| D534,448 S | 1/2007 | Shaffer, II et al. |
| 7,158,030 B2 | 1/2007 | Chung |
| 7,158,754 B2 | 1/2007 | Anderson |
| 7,160,258 B2 | 1/2007 | Imran et al. |
| D536,673 S | 2/2007 | Silber |
| 7,176,798 B2 | 2/2007 | Dimmer et al. |
| 7,183,914 B2 | 2/2007 | Norman et al. |
| 7,183,927 B2 | 2/2007 | Kolton et al. |
| 7,227,469 B2 | 6/2007 | Varner et al. |
| 7,245,893 B1 | 7/2007 | Husted et al. |
| 7,256,695 B2 | 8/2007 | Hamel et al. |
| 7,256,696 B2 | 8/2007 | Levin |
| 7,268,684 B2 | 9/2007 | Tethrake et al. |
| 7,269,047 B1 | 9/2007 | Fong et al. |
| 7,299,981 B2 | 11/2007 | Hickle et al. |
| D557,421 S | 12/2007 | Fleck et al. |
| D557,423 S | 12/2007 | Chen |
| D558,352 S | 12/2007 | Sanfilippo |
| 7,307,530 B2 | 12/2007 | Fabian et al. |
| D558,882 S | 1/2008 | Brady |
| 7,319,396 B2 | 1/2008 | Homanfar et al. |
| 7,319,397 B2 | 1/2008 | Chung et al. |
| 7,325,723 B2 | 2/2008 | Desjeux |
| 7,333,013 B2 | 2/2008 | Berger |
| 7,342,497 B2 | 3/2008 | Chung et al. |

(56) References Cited

U.S. PATENT DOCUMENTS

| | | | |
|---|---|---|---|
| 7,362,228 B2 | 4/2008 | Nycz et al. |
| D568,186 S | 5/2008 | Blair et al. |
| 7,382,255 B2 | 6/2008 | Chung |
| 7,397,364 B2 | 7/2008 | Govari |
| 7,399,899 B2 | 7/2008 | Fabian |
| 7,408,168 B1 | 8/2008 | Aufrichtig et al. |
| 7,420,468 B2 | 9/2008 | Fabian et al. |
| 7,423,535 B2 | 9/2008 | Chung et al. |
| 7,446,646 B2 | 11/2008 | Huomo |
| 7,449,614 B2 | 11/2008 | Ales, III |
| 7,464,713 B2 | 12/2008 | Fabian et al. |
| 7,465,847 B2 | 12/2008 | Fabian |
| 7,471,541 B2 | 12/2008 | Fong et al. |
| D584,414 S | 1/2009 | Lash et al. |
| 7,474,222 B2 | 1/2009 | Yang et al. |
| 7,492,257 B2 | 2/2009 | Tethrake et al. |
| 7,492,261 B2 | 2/2009 | Cambre et al. |
| 7,492,263 B2 | 2/2009 | Marsilio et al. |
| 7,508,308 B2 | 3/2009 | Chung |
| D590,342 S | 4/2009 | Dávila et al. |
| 7,513,425 B2 | 4/2009 | Chung |
| 7,541,933 B2 | 6/2009 | Volpi et al. |
| D598,110 S | 8/2009 | Phillips et al. |
| D598,114 S | 8/2009 | Cryan |
| 7,609,538 B1 | 10/2009 | Lee et al. |
| 7,644,016 B2 | 1/2010 | Nycz et al. |
| 7,696,877 B2 | 4/2010 | Barnes et al. |
| 7,769,422 B2 | 8/2010 | DiSilvestro et al. |
| 7,795,491 B2 | 9/2010 | Stewart et al. |
| 7,855,656 B2 | 12/2010 | Maschke |
| 7,876,097 B2 | 1/2011 | Greim |
| 7,898,420 B2 | 3/2011 | Blair et al. |
| 8,082,192 B2 | 12/2011 | Nycz et al. |
| 8,105,296 B2 | 1/2012 | Morris et al. |
| 8,111,162 B2 | 2/2012 | Barnes et al. |
| 8,181,860 B2 | 5/2012 | Fleck et al. |
| 8,193,938 B2 | 6/2012 | Halberthal et al. |
| 8,259,518 B2 | 9/2012 | Peng et al. |
| 8,279,068 B2 | 10/2012 | Morris et al. |
| 8,319,612 B2 | 11/2012 | Borcherding |
| 8,371,448 B1 | 2/2013 | Reaux |
| 8,454,613 B2 | 6/2013 | Tethrake et al. |
| 8,477,076 B1 | 7/2013 | Nero, Jr. et al. |
| 8,477,077 B1 | 7/2013 | Nero, Jr. et al. |
| 8,576,076 B2 | 11/2013 | Morris et al. |
| 8,780,660 B2 | 7/2014 | Peng |
| 8,872,662 B2 | 10/2014 | Halberthal et al. |
| 8,978,229 B2 | 3/2015 | Halberthal et al. |
| 8,985,446 B2 | 3/2015 | Fleck et al. |
| 8,994,358 B2 | 3/2015 | McElhinny et al. |
| 9,041,479 B2 | 5/2015 | Nero, Jr. et al. |
| 9,119,667 B2 | 9/2015 | Halberthal et al. |
| 2001/0030610 A1 | 10/2001 | Rochelle et al. |
| 2002/0011932 A1 | 1/2002 | Rodgers et al. |
| 2002/0032435 A1 | 3/2002 | Levin |
| 2002/0070863 A1 | 6/2002 | Brooking |
| 2002/0143320 A1 | 10/2002 | Levin |
| 2002/0165587 A1 | 11/2002 | Zhang et al. |
| 2002/0188259 A1 | 12/2002 | Hickle et al. |
| 2003/0004411 A1 | 1/2003 | Govari et al. |
| 2003/0052788 A1 | 3/2003 | Kwong-Tai Chung |
| 2003/0105394 A1 | 6/2003 | Fabian et al. |
| 2003/0111592 A1 | 6/2003 | Al-Ali |
| 2004/0008123 A1 | 1/2004 | Carrender et al. |
| 2004/0129279 A1 | 7/2004 | Fabian et al. |
| 2004/0137844 A1 | 7/2004 | Desjeux et al. |
| 2004/0138554 A1 | 7/2004 | Dimmer et al. |
| 2004/0250819 A1 | 12/2004 | Blair et al. |
| 2005/0110640 A1 | 5/2005 | Chung |
| 2005/0131397 A1 | 6/2005 | Levin |
| 2005/0154293 A1 | 7/2005 | Gisselberg et al. |
| 2005/0212673 A1 | 9/2005 | Forster |
| 2005/0247794 A1 | 11/2005 | Jones et al. |
| 2005/0249036 A1 | 11/2005 | Davies et al. |
| 2005/0267550 A1 | 12/2005 | Hess et al. |
| 2006/0047238 A1 | 3/2006 | Galdenzi et al. |
| 2006/0055537 A1 | 3/2006 | Jackson |
| 2006/0084934 A1 | 4/2006 | Frank |
| 2006/0106368 A1 | 5/2006 | Miller et al. |
| 2006/0109086 A1 | 5/2006 | Amtmann |
| 2006/0187044 A1 | 8/2006 | Fabian et al. |
| 2006/0202827 A1 | 9/2006 | Volpi et al. |
| 2006/0232407 A1 | 10/2006 | Ballard |
| 2006/0235488 A1 | 10/2006 | Nycz et al. |
| 2006/0241396 A1 | 10/2006 | Fabian et al. |
| 2006/0241399 A1 | 10/2006 | Fabian |
| 2006/0244597 A1 | 11/2006 | Tethrake et al. |
| 2006/0244652 A1 | 11/2006 | Tethrake et al. |
| 2006/0270933 A1 | 11/2006 | Benson et al. |
| 2007/0004994 A1 | 1/2007 | Sherman |
| 2007/0005141 A1 | 1/2007 | Sherman |
| 2007/0069866 A1* | 3/2007 | Schuessler ......... G06K 7/10198 340/10.4 |
| 2007/0109099 A1 | 5/2007 | Raphaeli et al. |
| 2007/0125392 A1 | 6/2007 | Olson, Jr. et al. |
| 2007/0152823 A1 | 7/2007 | Hirahara et al. |
| 2007/0209957 A1 | 9/2007 | Glenn et al. |
| 2007/0216062 A1 | 9/2007 | Frank |
| 2007/0238982 A1 | 10/2007 | Caylor, III |
| 2007/0239289 A1 | 10/2007 | Cambre et al. |
| 2007/0244470 A1 | 10/2007 | Barker, Jr. et al. |
| 2007/0265690 A1 | 11/2007 | Lichtenstein et al. |
| 2007/0270660 A1 | 11/2007 | Caylor, III et al. |
| 2007/0285249 A1 | 12/2007 | Blair et al. |
| 2008/0007411 A1 | 1/2008 | Levin |
| 2008/0021308 A1 | 1/2008 | Dimmer et al. |
| 2008/0024281 A1* | 1/2008 | Shimura ............... G06K 7/0008 340/10.3 |
| 2008/0051746 A1 | 2/2008 | Shen-Gunther |
| 2008/0086771 A1* | 4/2008 | Li ........................ H04L 9/3234 726/20 |
| 2008/0126122 A1 | 5/2008 | Warner et al. |
| 2008/0132860 A1 | 6/2008 | Smith et al. |
| 2008/0204245 A1* | 8/2008 | Blair ....................... A61B 5/06 340/572.1 |
| 2008/0231452 A1 | 9/2008 | Levin |
| 2008/0243404 A1 | 10/2008 | Banhegyesi |
| 2008/0272913 A1 | 11/2008 | Barnes et al. |
| 2008/0281190 A1 | 11/2008 | Petcavich et al. |
| 2008/0284570 A1* | 11/2008 | Ryoo .................... G06K 7/0008 340/10.1 |
| 2008/0296373 A1 | 12/2008 | Zmood et al. |
| 2009/0014518 A1 | 1/2009 | Stewart et al. |
| 2009/0051485 A1* | 2/2009 | Corry .................... G06K 17/00 340/5.8 |
| 2009/0267765 A1 | 10/2009 | Greene et al. |
| 2009/0315681 A1 | 12/2009 | Blair |
| 2010/0033309 A1 | 2/2010 | Blair |
| 2010/0108079 A1 | 5/2010 | Blair |
| 2010/0109848 A1 | 5/2010 | Blair et al. |
| 2011/0004276 A1 | 1/2011 | Blair et al. |
| 2011/0063078 A1* | 3/2011 | Souma ................. G06K 7/0095 340/10.1 |
| 2011/0181394 A1 | 7/2011 | Blair |
| 2012/0031547 A1 | 2/2012 | Halberthal et al. |
| 2013/0023225 A1 | 1/2013 | Weber |
| 2013/0199720 A1 | 8/2013 | Halberthal et al. |
| 2015/0164603 A1 | 6/2015 | Fleck et al. |
| 2015/0216610 A1 | 8/2015 | Augustine |
| 2015/0317555 A1 | 11/2015 | Dor et al. |

FOREIGN PATENT DOCUMENTS

| | | |
|---|---|---|
| CN | 101450096 A | 6/2009 |
| EP | 1 612 554 A1 | 1/2006 |
| EP | 2 087 850 A2 | 8/2009 |
| JP | 2009539478 A | 11/2009 |
| WO | 02/39917 A1 | 5/2002 |
| WO | 2004/008387 A1 | 1/2004 |
| WO | 2004/086997 A1 | 10/2004 |
| WO | 2006/060781 A1 | 6/2006 |
| WO | 2007/146091 A1 | 12/2007 |
| WO | 2008/024921 A1 | 2/2008 |
| WO | 2006/112709 A1 | 9/2008 |

(56) References Cited

FOREIGN PATENT DOCUMENTS

| WO | 2008/106552 A1 | 9/2008 |
| WO | 2008/133634 A1 | 11/2008 |
| WO | 2009/151946 A1 | 12/2009 |
| WO | 2009/154987 A1 | 12/2009 |

OTHER PUBLICATIONS

Blair et al., "Improved Apparatus and Method for Detecting Objects Using Tags and Wideband Detection Device," U.S. Appl. No. 60/811,376, filed Jun. 6, 2006, 16 pages.

Blair et al., "Method, Apparatus and Article for Detection of Transponder Tagged Objects, for Example During Surgery," U.S. Appl. No. 60/892,208, filed Feb. 28, 2007, 50 pages.

Blair et al., "Transponder Housing and Device to Mark Implements, Such As Surgical Implements, and Method of Using Same," U.S. Appl. No. 60/894,435, filed Mar. 12, 2007, 30 pages.

Blair, "Apparatus, Method, and Article for Detection and Identification of Multi-Mode Integral Transponder Tagged Objects," U.S. Appl. No. 61/056,229, filed May 27, 2008, 38 pages.

Barnes et al., "Method, Apparatus and Article for Detection of Transponder Tagged Objects, for Example During Surgery," U.S. Appl. No. 61/056,787, filed May 28, 2008, 60 pages.

Blair, "Transponder Device to Mark Implements, Such As Surgical Implements, and Method of Manufacturing and Using Same," U.S. Appl. No. 61/086,727, filed Aug. 6, 2008, 30 pages.

Barnes et al., "Method, Apparatus and Article for Detection of Transponder Tagged Objects, for Example During Surgery," U.S. Appl. No. 61/091,667, filed Aug. 25, 2008, 76 pages.

Blair, "Multi-Modal Transponder and Method and Apparatus to Detect Same," U.S. Appl. No. 61/102,749, filed Oct. 3, 2008, 48 pages.

Blair et al., "Method and Apparatus to Detect Transponder Tagged Objects, for Example During Surgery," U.S. Appl. No. 61/109,104, filed Oct. 28, 2008, 73 pages.

Blair, "Detectable Surgical Objects and Methods of Making Same," U.S. Appl. No. 61/109,142, filed Oct. 28, 2008, 47 pages.

Blair et al., "Method and Apparatus to Detect Transponder Tagged Objects, for Example During Medical Procedures," U.S. Appl. No. 61/242,704, filed Sep. 15, 2009, 127 pages.

Blair, "Transponder Device to Mark Implements, Such As Surgical Implements, and Method of Manufacturing and Using Same," U.S. Appl. No. 61/220,452, filed Jun. 25, 2009, 46 pages.

Blair, "Radio Opaque Device With Resonant Nanostructures," U.S. Appl. No. 61/163,813, filed Mar. 26, 2009, 47 pages.

Blair et al., "Method and Apparatus to Detect Transponder Tagged Objects, for Example During Surgery," U.S. Appl. No. 61/222,443, filed Jul. 1, 2009, 95 pages.

Blair et al., "Method and Apparatus to Detect Transponder Tagged Objects and to Communicate With Medical Telemetry Devices, for Example During Surgery," U.S. Appl. No. 61/222,847, filed Jul. 2, 2009, 122 pages.

Blair, "Transponder Device to Mark Implements, Such As Surgical Implements, and Method of Manufacturing and Using Same," U.S. Appl. No. 61/224,323, filed Jul. 9, 2009, 57 pages.

Blair et al., "Method and Apparatus to Detect Transponder Tagged Objects and to Communicate With Medical Telemetry Devices, for Example During Medical Procedures," U.S. Appl. No. 61/242,699, filed Sep. 15, 2009, 158 pages.

Blair, "Method and Apparatus to Account for Transponder Tagged Objects Used During Medical Procedures," U.S. Appl. No. 61/263,726, filed Nov. 23, 2009, 78 pages.

Barnes et al., "Design for a FET based 1 MHz, 10kV Pulse Generator," Pulsed Power Conference, Digest of Technical Papers, Tenth IEEE International, 2:1335-1340, 1995.

Clearcount Medical Solutions, "The SmartSponge System," Downloaded from http://clearcount.com on Oct. 20, 2009, 7 pages.

Macario et al., "Initial Clinical Evaluation of a Handheld Device for Detecting Retained Surgical Gauze Sponges Using Radiofrequency Identification Technology," Arch Surg 141:659-662, Jul. 2006.

International Search Report, mailed Jan. 4, 2010, for PCT/US2009/045312, 3 pages.

Written Opinion, mailed Jan. 4, 2010, for PCT/US2009/045312, 3 pages.

International Search Report, mailed Dec. 23, 2014, for PCT/US2014/045942, 3 pages.

Written Opinion, mailed Dec. 23, 2014, for PCT/US2014/045942, 7 pages.

Extended European Search Report dated Jul. 30, 2015 for corresponding EP Application No. 14176398.7-1958, 7 pages.

Reza et al., "RFID Transponder Collision Control Algorithm," *Wireless Pers. Commun.* 59:689-711, 2011.

Haldor Advance Technologies, "Haldor Advanced Technologies Releases a Breakthrough New Sponge Management Solution: Modular, Mobile, Wireless, and Tailored per Use-case and Requirements," Sep. 8, 2015, retrieved from http://ww.1.prweb.com/prfiles/2015/09/06/12938762/ORLocate%205Sponge%20Solution-September%202015.pdf, 2 pages.

\* cited by examiner

METHOD, APPARATUS AND ARTICLE FOR DETECTION OF TRANSPONDER TAGGED OBJECTS, FOR EXAMPLE DURING SURGERY

BACKGROUND

1. Field

This disclosure generally relates to the detection of the presence or absence of objects tagged with transponders, which may, for example, allow the detection of surgical objects during surgery.

2. Description of the Related Art

It is often useful or important to be able to determine the presence or absence of an object.

For example, it is important to determine whether objects associated with surgery are present in a patient's body before completion of the surgery. Such objects may take a variety of forms. For example, the objects may take the form of instruments, for instance scalpels, scissors, forceps, hemostats, and/or clamps. Also for example, the objects may take the form of related accessories and/or disposable objects, for instance surgical sponges, gauzes, and/or pads. Failure to locate an object before closing the patient may require additional surgery, and in some instances may have serious adverse medical consequences.

Some hospitals have instituted procedures which include checklists or requiring multiple counts to be performed to track the use and return of objects during surgery. Such a manual approach is inefficient, requiring the time of highly trained personnel, and is prone to error.

Another approach employs transponders and a wireless interrogation and detection system. Such an approach employs wireless transponders which are attached to various objects used during surgery. The interrogation and detection system includes a transmitter that emits pulsed wideband wireless signals (e.g., radio or microwave frequency) and a detector for detecting wireless signals returned by the transponders in response to the emitted pulsed wideband signals. Such an automated system may advantageously increase accuracy while reducing the amount of time required of highly trained and highly compensated personnel. Examples of such an approach are discussed in U.S. Pat. No. 6,026,818, issued Feb. 22, 2000, and U.S. Patent Publication No. US 2004/0250819, published Dec. 16, 2004.

Commercial implementation of such an automated system requires that the overall system be cost competitive and highly accurate. In particular, false negatives must be avoided to ensure that objects are not mistakenly left in the patient. Some facilities may wish to install a single interrogation and detection system in each surgery theater, while other facilities may move an interrogation and detection system between multiple surgical theaters. In either case, the overall system will require a large number of transponders, since at least one transponder is carried, attached or otherwise coupled to each object which may or will be used in surgery. Consequently, the transponders must be inexpensive. However, inexpensive transponders typically have a relatively large variation in the frequency of signals they emit, making it difficult to accurately detect the signals returned by the transponders. This may be particularly difficult in some environments which are noisy with respect to the particular resonant frequencies of the transponders. Consequently, a new approach to detection of the presence and absence of transponder that facilitates the use of inexpensive transponders is highly desirable.

BRIEF SUMMARY

A method of operating a transponder detection device that includes at least one processor, at least one nontransitory processor-readable medium communicatively coupled to the at least one processor and which stores at least one of instructions or data executable by the at least one processor may be summarized as including: during each of a first plurality of successive interrogation cycles, emitting a periodic electromagnetic interrogation signal during a transmit portion of the interrogation cycle; receiving electromagnetic signals during a receive response portion of the interrogation cycle that follows the transmit portion of the interrogation cycle; and waiting a first delay period before a start of each of the successive interrogation cycles of the first plurality of interrogation cycles, the first delay period for the first plurality of interrogation cycles equal to a first fraction of a nominal tag response signal period; during each of a second plurality of successive interrogation cycles, emitting a periodic electromagnetic interrogation signal during a transmit portion of the interrogation cycle; receiving electromagnetic signals during a receive response portion of the interrogation cycle that follows the transmit portion of the interrogation cycle; and waiting a second delay period before a start of each of the successive interrogation cycles in the second plurality of interrogation cycles, the second delay period for the second plurality of interrogation cycles equal to a second fraction of the nominal tag response signal period, the second fraction of the nominal tag response signal period different from the first fraction of the nominal tag response signal period.

The method may further include: during each of a third plurality of successive interrogation cycles, emitting a periodic electromagnetic interrogation signal during a transmit portion of the interrogation cycle; receiving electromagnetic signals during a receive response portion of the interrogation cycle that follows the transmit portion of the interrogation cycle; and waiting a third delay period before a start of each of the successive interrogation cycles in the third plurality of interrogation cycles, the third delay period for the third plurality of interrogation cycles equal to a third fraction of the nominal tag response signal period, the third fraction of the nominal tag response signal period different from the first fraction of the nominal tag response signal period and the second fraction of the nominal tag response signal period. Waiting a first delay period before a start of each of the successive interrogation cycles of the first plurality of interrogation cycles may include waiting a first delay period before a start of each of the successive interrogation cycles of the first plurality of interrogation cycles, the first delay period less than the nominal tag response signal period, and waiting a second delay period before a start of each of the successive interrogation cycles in the second plurality of interrogation cycles may include waiting a second delay period before a start of each of the successive interrogation cycles in the second plurality of interrogation cycles, the second delay period less than the nominal tag response signal period. Waiting a second delay period before a start of each of the successive interrogation cycles in the second plurality of interrogation cycles may include waiting a second delay period before a start of each of the successive interrogation cycles in the second plurality of interrogation cycles, one of the first delay period and the second delay period an integer multiple of the other of the first delay period and the second delay period. Waiting a first delay period before a start of each of the successive interrogation cycles of the first plurality of interrogation cycles may include waiting a first delay period before a start of each of the successive interrogation cycles of the first plurality of interrogation cycles, the first delay period less than half the nominal tag response signal period, and waiting a second delay period before a start of each of the successive interrogation cycles in the second plurality of interrogation cycles may include waiting a second delay period before a start of each of the successive interrogation cycles in the second plurality of interrogation cycles, the second delay period less than half the nominal tag response signal period. Waiting a first delay period before a start of each of the successive interrogation cycles of the first plurality of interrogation cycles may include waiting a first delay period before a start of each of the successive interrogation cycles of the first plurality of interrogation cycles, the first delay period greater than the nominal tag response signal period, and waiting a second delay period before a start of each of the successive interrogation cycles in the second plurality of interrogation cycles may include waiting a second delay period before a start of each of the successive interrogation cycles in the second plurality of interrogation cycles, the second delay period greater than the nominal tag response signal period. Waiting a first delay period before a start of each of the successive interrogation cycles of the first plurality of interrogation cycles may include waiting a first delay period before a start of each of the successive interrogation cycles of the first plurality of interrogation cycles, the first delay period approximately equal to zero seconds, and waiting a second delay period before a start of each of the successive interrogation cycles in the second plurality of interrogation cycles may include waiting a second delay period before a start of each of the successive interrogation cycles in the second plurality of interrogation cycles, the second delay period less than the nominal tag response signal period. Waiting a second delay period before a start of each of the successive interrogation cycles in the second plurality of interrogation cycles may include waiting a second delay period before a start of each of the successive interrogation cycles in the second plurality of interrogation cycles, the second delay period greater than the first delay period. The method may further include: during each of the plurality of interrogation cycles, before the receive response portion of the interrogation cycle, waiting a fixed recovery time after the transmit portion of the interrogation cycle, the fixed recovery time having a duration that provides synchronization between the transmit portion and the receive response portion of each interrogation cycle. The method may further include: determining the presence or absence of a transponder based at least in part on a number of measurements of the electromagnetic signals received during the first plurality of interrogation cycles and the second plurality of interrogation cycles. Determining the presence or absence of a transponder may be based at least in part on a frequency of the electromagnetic signals received during the interrogation cycle being within a defined frequency range. The defined frequency range may extend from about 137 kHz to about 160 kHz. Determining the presence or absence of a transponder may be based at least in part on a Q value of the electromagnetic signals received during the interrogation cycle. Determining the presence or absence of a transponder may be based at least in part on a Q value of the electromagnetic signals received during the interrogation cycle being at least equal to a threshold Q value. The threshold Q value may be 35. The method may further include: determining the presence or absence of a transponder based at least in part on a signal detection threshold. The method may further include: receiving electromagnetic signals during a noise detection portion; determining a noise value indicative of a noise level that corresponds to a number of measurements of the electromagnetic signals received during the noise detection portion; adjusting a signal detection threshold based at least in part on the determined noise value; and determining the presence or absence of a transponder based at least in part on a number of measurements of the electromagnetic signals received during the first plurality of interrogation cycles and the second plurality of interrogation cycles and the adjusted signal detection threshold. Determining the presence or absence of a transponder may include comparing a maximum value of a plurality of matched filter outputs with the adjusted signal detection threshold. Adjusting a signal detection threshold based at least in part on the determined noise value may include adjusting the signal detection threshold to be approximately twice the determined noise value. The method may further include: determining if an output of at least one matched filter during the noise detection portion exceeds a noise fault threshold indicative of a noise fault. Emitting the electromagnetic interrogation signal during a transmit portion of the interrogation cycle may include emitting an electromagnetic interrogation signal in at least one of a 136 kHz band, a 139 kHz band, a 142 kHz band, a 145 kHz band, a 148 kHz band, a 151 kHz band or a 154 kHz band. The method may further include: ignoring any electromagnetic signals received during a recovery portion of the interrogation cycle that precedes the receive response portion of the interrogation cycle. The method may further include: dumping energy from an antenna circuit during a dump portion of the interrogation cycle that precedes the receive response portion of the interrogation cycle. Receiving electromagnetic signals during a receive response portion of the interrogation cycle that follows the transmit portion of the interrogation cycle may include receiving unmodulated electromagnetic signals during the receive response portion of the interrogation cycle.

A method of operating a transponder detection device that includes at least one processor, at least one nontransitory processor-readable medium communicatively coupled to the at least one processor and which stores at least one of instructions or data executable by the at least one processor may be summarized as including: obtaining a number of subsamples, each of the subsamples associated with a respective delay period equal to a respective fraction of a nominal tag response signal period, the respective fractions different from one another, each of the number of subsamples obtained by: during each of a plurality of successive interrogation cycles associated with each of the number of subsamples, emitting a periodic electromagnetic interrogation signal during a transmit portion of the interrogation cycle; receiving electromagnetic signals during a receive response portion of the interrogation cycle that follows the transmit portion of the interrogation cycle; and waiting the delay period of the one of the number of subsamples to which the interrogation cycle is associated before a start of each of the successive interrogation cycles of the plurality of interrogation cycles.

Waiting a delay period before a start of each of the successive interrogation cycles of the plurality of interrogation cycles may include waiting a delay period before a start of each of the successive interrogation cycles of the plurality of interrogation cycles, the delay period for each of the number of subsamples between zero seconds and the nominal tag response signal period. Waiting a delay period before a start of each of the successive interrogation cycles of the plurality of interrogation cycles may include waiting a delay period before a start of each of the successive interrogation cycles of the plurality of interrogation cycles, the delay period for at least one of the number of subsamples being a duration between the nominal tag response signal period and twice the nominal tag response signal period. Waiting a delay period before a start of each of the successive interrogation cycles of the plurality of interrogation cycles may include waiting a delay period before a start of each of the successive interrogation cycles of the plurality of interrogation cycles and, for each successive pair of subsamples, the delay period associated with a first successive one of the pairs of subsamples is less than the delay period associated with a next successive one of the pairs of subsamples. Waiting a delay period before a start of each of the successive interrogation cycles of the plurality of interrogation cycles may include waiting a delay period before a start of each of the successive interrogation cycles of the plurality of interrogation cycles and, for each successive pair of subsamples, the delay period associated with a first successive one of the pairs of subsamples may be less than the delay period associated with a next successive one of the pairs of subsamples by a duration approximately equal to the nominal tag response signal period divided by the number of subsamples. Waiting a delay period before a start of each of the successive interrogation cycles of the plurality of interrogation cycles may include waiting a delay period before a start of each of the successive interrogation cycles of the plurality of interrogation cycles, and the delay period associated with each subsample differs from the delay period for the other subsamples by less than the nominal tag response signal period. Waiting a delay period before a start of each of the successive interrogation cycles of the plurality of interrogation cycles may include waiting a delay period before a start of each of the successive interrogation cycles of the plurality of interrogation cycles, and the delay period associated with each subsample may be approximately an integer multiple of the nominal tag response signal period divided by the number of subsamples. The method may further include: during each of the plurality of interrogation cycles, before the receive response portion of the interrogation cycle, waiting a fixed recovery time after the transmit portion of the interrogation cycle, the fixed recovery time having a duration determined to provide synchronization between the transmit portion and the receive response portion of each interrogation cycle. The transponder detection device may include a plurality of antennas, the method may further include: obtaining a number of subsamples for each of the plurality of antennas. The method may further include: determining the presence or absence of a transponder based at least in part on a number of measurements of the electromagnetic signals received during the plurality of interrogation cycles of at least one of the number of subsamples. Determining the presence or absence of a transponder may be based at least in part on a frequency of the electromagnetic signals received during the interrogation cycle being within a defined frequency range. The defined frequency range may extend from about 137 kHz to about 160 kHz. Determining the presence or absence of a transponder may be based at least in part on a Q value of the electromagnetic signals received during the interrogation cycle. Determining the presence or absence of a transponder may be based at least in part on a Q value of the electromagnetic signals received during the interrogation cycle being at least equal to a threshold Q value. The threshold Q value may be 35. The method may further include: determining the presence or absence of a transponder based at least in part on a signal detection threshold. Determining the presence or absence of a transponder based at least in part on a number of measurements of the electromagnetic signals received during the plurality of interrogation cycles of at least one of the number of subsamples may include determining whether at least two of the number of subsamples are above a signal detection threshold. The method may further include: receiving electromagnetic signals during a noise detection portion; determining a noise value indicative of a noise level that corresponds to a number of measurements of the electromagnetic signals received during the noise detection portion; adjusting a signal detection threshold based at least in part on the determined noise value; and determining the presence or absence of a transponder based at least in part on a number of measurements of the electromagnetic signals received during the plurality of interrogation cycles of at least one of the number of subsamples and the adjusted signal detection threshold. Determining the presence or absence of a transponder may include comparing a maximum value of a plurality of matched filter outputs with the adjusted signal detection threshold. Adjusting a signal detection threshold based at least in part on the determined noise value may include adjusting the signal detection threshold to be approximately twice the determined noise value. The method may further include: determining if an output of at least one matched filter during the noise detection portion exceeds a noise fault threshold indicative of a noise fault. Emitting the electromagnetic interrogation signal during a transmit portion of the interrogation cycle may include emitting an electromagnetic interrogation signal in at least one of a 136 kHz band, a 139 kHz band, a 142 kHz band, a 145 kHz band, a 148 kHz band, a 151 kHz band or a 154 kHz band. The method may further include: ignoring any electromagnetic signals received during a recovery portion of the interrogation cycle that precedes the receive response portion of the interrogation cycle. The method may further include: dumping energy from an antenna circuit during a dump portion of the interrogation cycle that precedes the receive response portion of the interrogation cycle. Receiving electromagnetic signals during a receive response portion of the interrogation cycle that follows the transmit portion of the interrogation cycle may include receiving unmodulated electromagnetic signals during the receive response portion of the interrogation cycle.

A method of operating a transponder detection device that includes at least one processor, at least one nontransitory processor-readable medium communicatively coupled to the at least one processor and which stores at least one of instructions or data executable by the at least one processor, and one or more antennas may be summarized as including: for each of the one or more antennas, obtaining a first set of subsamples, each of the subsamples associated with a respective delay period equal to a respective fraction of a nominal tag response signal period, the respective fractions different from one another, each of the subsamples in the first set of subsamples obtained by: during each of a plurality of successive interrogation cycles associated with each subsample in the first set of subsamples, emitting a first periodic electromagnetic interrogation signal during a transmit portion of the interrogation cycle, the first electromagnetic interrogation signal having a first interrogation signal frequency; receiving electromagnetic signals during a receive response portion of the interrogation cycle that follows the transmit portion of the interrogation cycle; and waiting the delay period of the one of the number of subsamples in the first set of subsamples to which the interrogation cycle is associated before a start of each of the successive interrogation cycles of the plurality of interrogation cycles; obtaining a second set of subsamples, each of the subsamples associated with a respective delay period equal to a respective fraction of a nominal tag response signal period, the respective fractions different from one another, each of the subsamples in the second set of subsamples obtained by: during each of a plurality of successive interrogation cycles associated with each subsample in the second set of subsamples, emitting a second periodic electromagnetic interrogation signal during a transmit portion of the interrogation cycle, the second electromagnetic interrogation signal having a second interrogation signal frequency different from the first interrogation signal frequency; receiving electromagnetic signals during a receive response portion of the interrogation cycle that follows the transmit portion of the interrogation cycle; and waiting a delay period of the one of the number of subsamples in the second set of subsamples to which the interrogation cycle is associated before a start of each of the successive interrogation cycles of the plurality of interrogation cycles.

A method of operating a transponder detection device that includes at least one processor, at least one nontransitory processor-readable medium communicatively coupled to the at least one processor and which stores at least one of instructions or data executable by the at least one processor, may be summarized as including: during each of a plurality of interrogation cycles, emitting a periodic electromagnetic interrogation signal during a transmit portion of the interrogation cycle; receiving electromagnetic signals during a receive response portion of the interrogation cycle that follows the transmit portion of the interrogation cycle; and waiting a delay period before a start of each of the successive interrogation cycles of the plurality of interrogation cycles; wherein the interrogation cycles in the plurality of interrogation cycles are grouped into a number of subsamples each including a plurality of successive interrogation cycles, and the delay periods for interrogation cycles within a first one of the number of subsamples are equal to each other and equal to a first fraction of a nominal tag response signal period, and the delay periods for interrogation cycles within a second one of the number of subsamples are equal to each other and equal to a second fraction of the nominal tag response signal period, the second fraction different from the first fraction.

The first fraction and the second fraction may be approximately equal to an integer multiple of the number of subsamples divided by the nominal tag response signal period.

A transponder detection device may be summarized as including: an antenna; a processor operatively coupled to the antenna; and a nontransitory processor-readable medium communicatively coupled to the processor and that stores at least one of instructions or data executable by the processor, which cause the processor to: execute a first plurality of successive interrogation cycles wherein, during each of the first plurality of successive interrogation cycles the transponder detection device, emits a periodic electromagnetic interrogation signal during a transmit portion of the interrogation cycle; receives electromagnetic signals during a receive response portion of the interrogation cycle that follows the transmit portion of the interrogation cycle; and waits a first delay period before a start of each of the successive interrogation cycles of the plurality of interrogation cycles, the first delay period for the first plurality of interrogation cycles equal to a first fraction of a nominal tag response signal period; execute a second plurality of successive interrogati the processor further on cycles wherein, during each of the second plurality of successive interrogation cycles the transponder detection device, emits a periodic electromagnetic interrogation signal during a transmit portion of the interrogation cycle; receives electromagnetic signals during a receive response portion of the interrogation cycle that follows the transmit portion of the interrogation cycle; and waits a second delay period before a start of each of the successive interrogation cycles of the plurality of interrogation cycles, the second delay period for the second plurality of interrogation cycles equal to a second fraction of the nominal tag response signal period, the second fraction of the nominal tag response signal period different from the first fraction of the nominal tag response signal period.

The processor may further: execute a third plurality of successive interrogation cycles wherein, during each of the third plurality of successive interrogation cycles the transponder detection device, emits a periodic electromagnetic interrogation signal during a transmit portion of the interrogation cycle; receives electromagnetic signals during a receive response portion of the interrogation cycle that follows the transmit portion of the interrogation cycle; and waits a third delay period before a start of each of the successive interrogation cycles of the third plurality of interrogation cycles, the third delay period for the third plurality of interrogation cycles equal to a third fraction of the nominal tag response signal period, the third fraction of the nominal tag response signal period different from the first fraction of the nominal tag response signal period and the second fraction of the nominal tag response signal period. The first delay period and the second delay period may each be less than the nominal tag response signal period. The first delay period and the second delay period may each be greater than the nominal tag response signal period. The first delay period may be approximately equal to zero seconds and the second delay period may be less than the nominal tag response signal period. The second delay period may be greater than the first delay period. One of the first delay period and the second delay period an integer multiple of the other of the first delay period and the second delay period. The first delay period and the second delay period may each be less than half the nominal tag response signal period. During each of the plurality of interrogation cycles, before the receive response portion of the interrogation cycle, the processor may further: wait a fixed recovery time after the transmit portion of the interrogation cycle, the fixed recovery time having a duration determined to provide synchronization between the transmit portion and the receive response portion of each interrogation cycle. The processor may further: determine the presence or absence of a transponder based at least in part on a number of measurements of the electromagnetic signals received during the first plurality of interrogation cycles and the second plurality of interrogation cycles. The processor may further: determine the presence or absence of a transponder based at least in part on a frequency of the electromagnetic signals received during the interrogation cycle being within a defined frequency range. The defined frequency range may extend from about 137 kHz to about 160 kHz. The processor may further: determine the presence or absence of a transponder based at least in part on a Q value of the electromagnetic signals received during the interrogation cycle. The processor may further: determine the presence or absence of a transponder based at least in part on a Q value of the electromagnetic signals received during the interrogation cycle being at least equal to a threshold Q value. The threshold Q value may be 35. The processor may further: determine the presence or absence of a transponder based at least in part on a signal detection threshold. The processor may further: receive electromagnetic signals during a noise detection portion; determine a noise value indicative of a noise level that corresponds to a number of measurements of the electromagnetic signals received during the noise detection portion; adjust a signal detection threshold based at least in part on the determined noise value; and determine the presence or absence of a transponder based at least in part on a number of measurements of the electromagnetic signals received during the first plurality of interrogation cycles and the second plurality of interrogation cycles and the adjusted signal detection threshold. The processor may further: compare a maximum value of a plurality of matched filter outputs with the adjusted signal detection threshold. The processor may further: adjust the signal detection threshold to be approximately twice the determined noise value. The processor may further: determine if an output of at least one matched filter during the noise detection portion exceeds a noise fault threshold indicative of a noise fault. The electromagnetic interrogation signal may be in at least one of a 136 kHz band, a 139 kHz band, a 142 kHz band, a 145 kHz band, a 148 kHz band, a 151 kHz band or a 154 kHz band. The processor may further: ignore any electromagnetic signals received during a recovery portion of the interrogation cycle that precedes the receive response portion of the interrogation cycle. The transponder detection device may further include: an antenna circuit coupled to the antenna; wherein the processor further causes energy to be dumped from the antenna circuit during a dump portion of the interrogation cycle that precedes the recovery portion of the interrogation cycle. The electromagnetic signals received during the receive response portion of the interrogation cycle may be unmodulated electromagnetic signals.

A transponder detection device may be summarized as including: an antenna; a processor operatively coupled to the antenna; and a nontransitory processor-readable medium communicatively coupled to the processor and that stores at least one of instructions or data executable by the processor, which cause the processor to: obtain a number of subsamples, each of the subsamples associated with a respective delay period equal to a respective fraction of a nominal tag response signal period, the respective fractions different from one another, each of the number of subsamples obtained by: during each of a plurality of successive interrogation cycles associated with each of the number of subsamples, the transponder detection device, emits via the antenna a periodic electromagnetic interrogation signal during a transmit portion of the interrogation cycle; receives via the antenna electromagnetic signals during a receive response portion of the interrogation cycle that follows the transmit portion of the interrogation cycle; and waits a delay period of the one of the number of subsamples to which the interrogation cycle is associated before a start of each of the successive interrogation cycles of the plurality of interrogation cycles.

The delay period for each of the number of subsamples may be between zero seconds and the nominal tag response signal period. The delay period for at least one of the number of subsamples may have a duration between the nominal tag response signal period and twice the nominal tag response signal period. For each successive pair of subsamples, the delay period associated with a first successive one of the pairs of subsamples may be less than the delay period associated with a next successive one of the pairs of subsamples. For each successive pair of subsamples, the delay period associated with a first successive one of the pairs of subsamples may be less than the delay period associated with a next successive one of the pairs of subsamples by a duration approximately equal to the nominal tag response signal period divided by the number of subsamples. The delay period associated with each subsample may differ from the delay period for the other subsamples by less than the nominal tag response signal period. The delay period associated with each subsample may be approximately an integer multiple of the nominal tag response signal period divided by the number of subsamples. During each of the plurality of interrogation cycles in each of the number of subsamples, before the receive response portion of the interrogation cycle, the processor may further: wait a fixed recovery time after the transmit portion of the interrogation cycle, the fixed recovery time having a duration determined to provide synchronization between the transmit portion and the receive response portion of each interrogation cycle. The transponder detection device may further include: a plurality of antennas operatively coupled to the antenna, and the processor may further: obtain a number of subsamples for each of the plurality of antennas. The processor may further: determine the presence or absence of a transponder based at least in part on a number of measurements of the electromagnetic signals received during the plurality of interrogation cycles of at least one of the number of subsamples. The processor may further: determine the presence or absence of a transponder based at least in part on a frequency of the electromagnetic signals received during the interrogation cycle being within a defined frequency range. The defined frequency range may extend from about 137 kHz to about 160 kHz. The processor may further: determine the presence or absence of a transponder based at least in part on a Q value of the electromagnetic signals received during the interrogation cycle. The processor may further: determine the presence or absence of a transponder based at least in part on a Q value of the electromagnetic signals received during the interrogation cycle being at least equal to a threshold Q value. The threshold Q value may be 35. The processor may further: determine the presence or absence of a transponder based at least in part on a signal detection threshold. The processor may further: determine whether at least two of the number of subsamples are above a signal detection threshold. The processor may further: receive electromagnetic signals during a noise detection portion; determine a noise value indicative of a noise level that corresponds to a number of measurements of the electromagnetic signals received during the noise detection portion; adjust a signal detection threshold based at least in part on the determined noise value; and determine the presence or absence of a transponder based at least in part on a number of measurements of the electromagnetic signals received during the plurality of interrogation cycles of at least one of the number of subsamples and the adjusted signal detection threshold. The processor may further: compare a maximum value of a plurality of matched filter outputs with the adjusted signal detection threshold. The processor may further: adjust the signal detection threshold to be approximately twice the determined noise value. The processor may further: determine if an output of at least one matched filter during the noise detection portion exceeds a noise fault threshold indicative of a noise fault. The electromagnetic interrogation signal may be in at least one of a 136 kHz band, a 139 kHz band, a 142 kHz band, a 145 kHz band, a 148 kHz band, a 151 kHz band or a 154 kHz band. The processor may further: ignore any electromagnetic signals received during a recovery portion of the interrogation cycle that precedes the receive response portion of the interrogation cycle. The transponder detection device may further include: an antenna circuit coupled to the antenna; wherein the processor may further cause energy to be dumped from the antenna circuit during a dump portion of the interrogation cycle that precedes the recovery portion of the interrogation cycle. The electromagnetic signals received during the receive response portion of the interrogation cycle may be unmodulated electromagnetic signals.

A transponder detection device may be summarized as including: one or more antennas; a processor operatively coupled to the one or more antennas; and a nontransitory processor-readable medium communicatively coupled to the processor and that stores at least one of instructions or data executable by the processor, which cause the processor to: for each of the one or more antennas, obtain a first set of subsamples, each of the subsamples associated with a respective delay period equal to a respective fraction of a nominal tag response signal period, the respective fractions different from one another, each of the subsamples in the first set of subsamples obtained by: during each of a plurality of interrogation cycles in each subsample in the first set of subsamples, the transponder detection device, emits a first periodic electromagnetic interrogation signal during a transmit portion of the interrogation cycle, the first electromagnetic interrogation signal having a first interrogation signal frequency; receives electromagnetic signals during a receive response portion of the interrogation cycle that follows the transmit portion of the interrogation cycle; and waits a delay period of the one of the number of subsamples to which the interrogation cycle is associated before a start of each of the successive interrogation cycles of the plurality of interrogation cycles; obtain a second set of subsamples, each of the subsamples associated with a respective delay period equal to a respective fraction of a nominal tag response signal period, the respective fractions different from one another, each of the subsamples in the second set of subsamples obtained by: during each of a plurality of interrogation cycles in each subsample in the second set of subsamples, the transponder detection device, emits a second periodic electromagnetic interrogation signal during a transmit portion of the interrogation cycle, the second electromagnetic interrogation signal having a second interrogation signal frequency different from the first interrogation signal frequency; receives electromagnetic signals during a receive response portion of the interrogation cycle that follows the transmit portion of the interrogation cycle; and waits a delay period of the one of the number of subsamples to which the interrogation cycle is associated before a start of each of the successive interrogation cycles of the plurality of interrogation cycles.

BRIEF DESCRIPTION OF THE SEVERAL VIEWS OF THE DRAWING(S)

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

Figure 8:
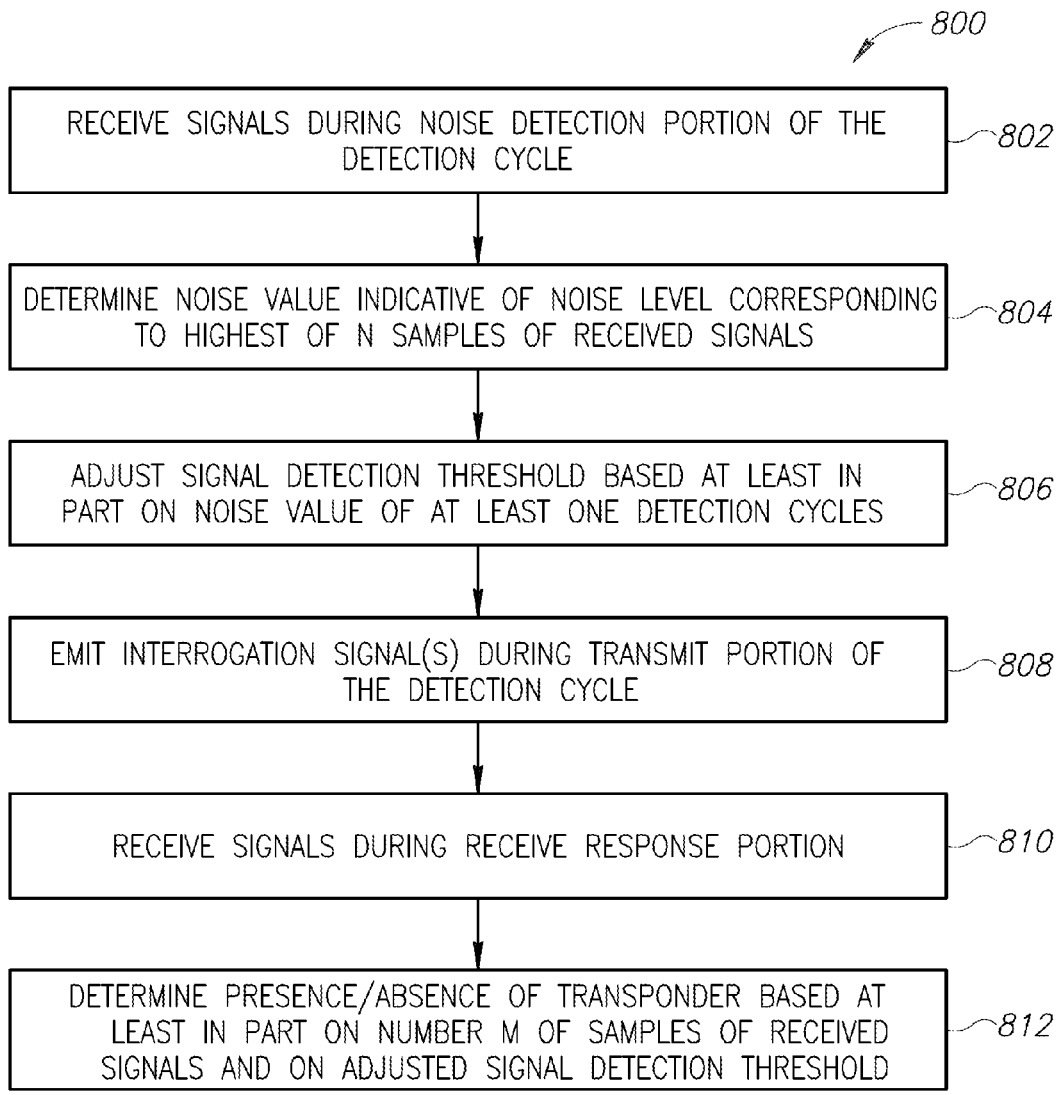

FIG. 8 is a flow diagram showing a method of operating an interrogation and detection system according to one illustrated embodiment, including receiving electromagnetic signals, for example unmodulated electromagnetic signals, determining a noise value, adjusting signal detection threshold, emitting interrogations signals, receiving electromagnetic signals, and determining a presence or absence of a transponder based at least in part on the adjusted signal detection threshold.

Figure 9:
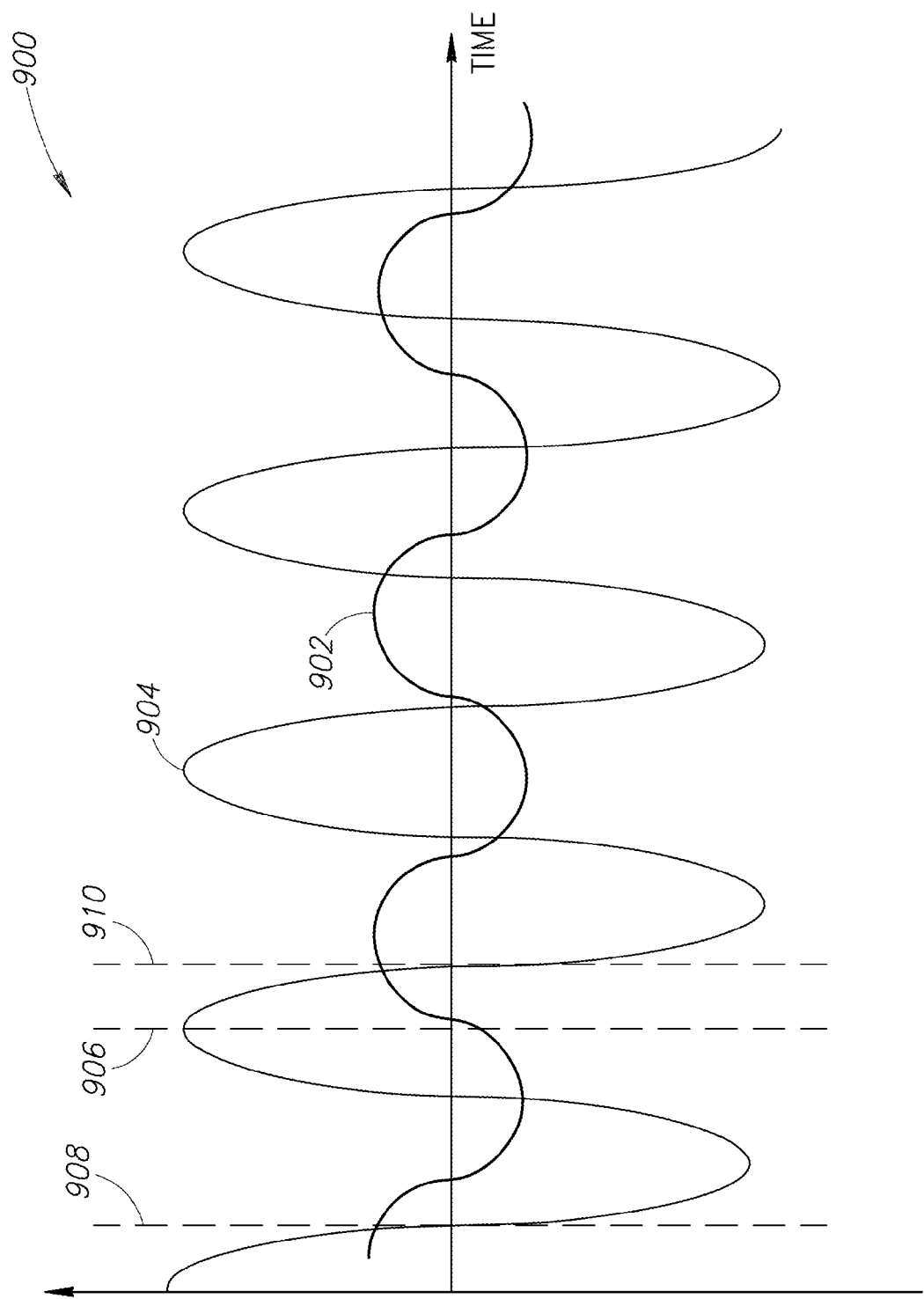

FIG. 9 is a graph showing noise and signal levels when the signal is sampled using subsample scan cycles, according to one illustrated embodiment.

Figure 10:
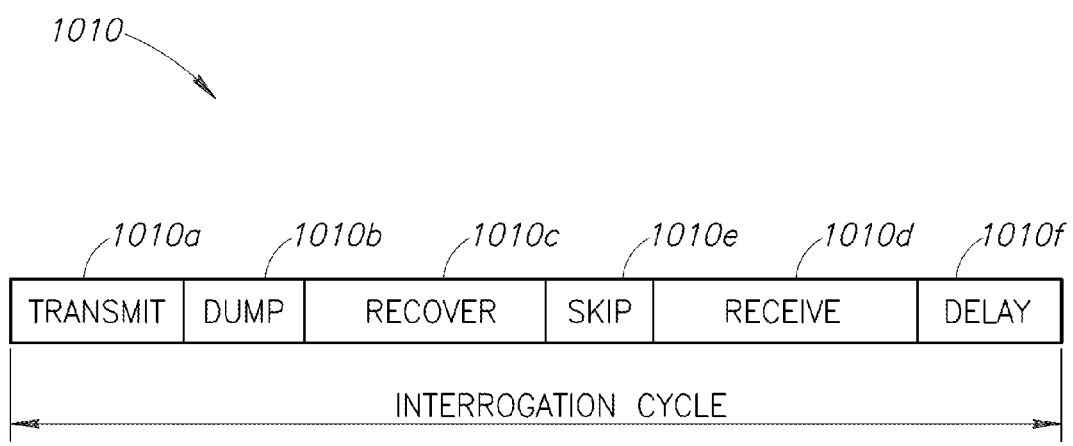

FIG. 10 is a timing diagram illustrating interrogation cycle timing, according to one illustrated embodiment.

Figure 11A:
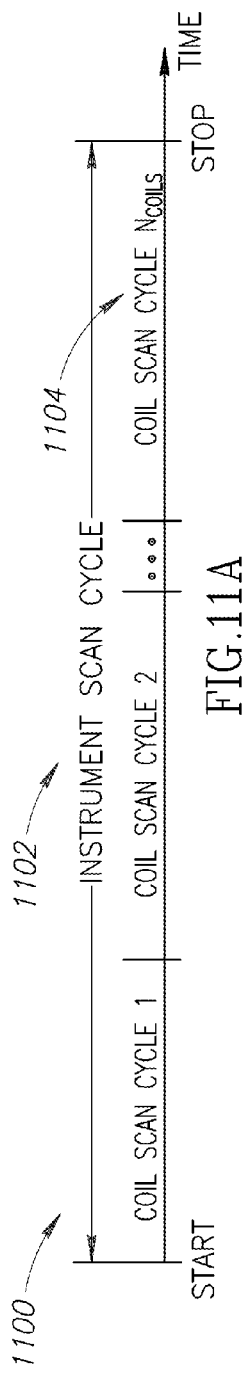

FIG. 11A is a timing diagram illustrating a scan cycle, according to one illustrated embodiment.

Figure 11B:
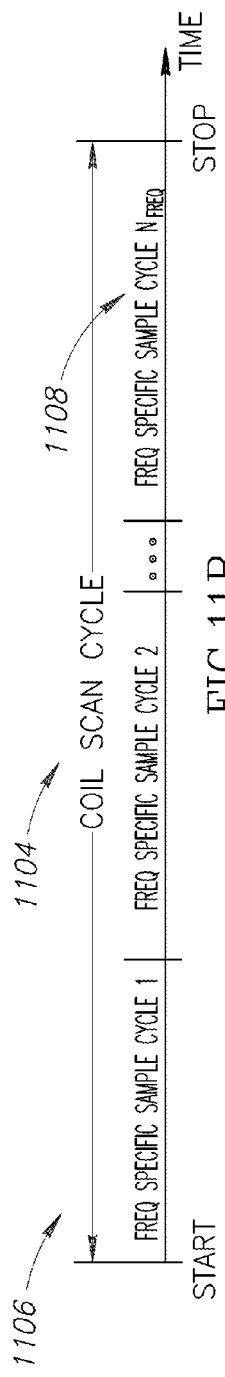

FIG. 11B is a timing diagram illustrating a coil scan cycle, according to one illustrated embodiment.

Figure 11C:
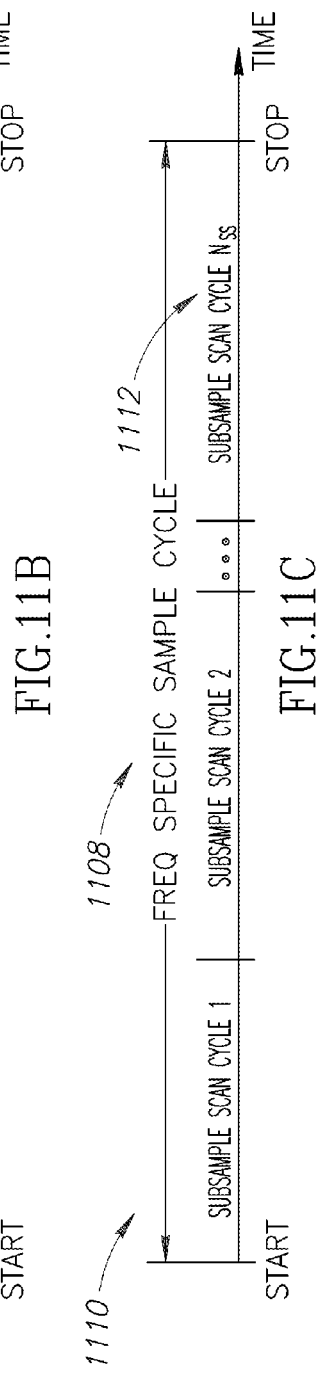

FIG. 11C is a timing diagram illustrating a frequency specific sample cycle, according to one illustrated embodiment.

Figure 11D:
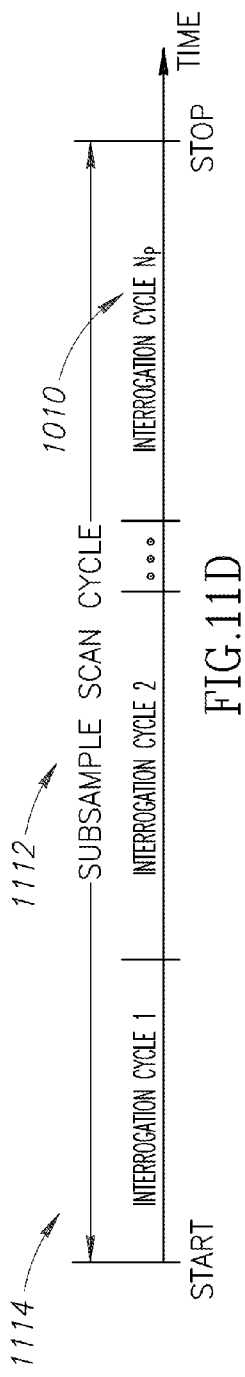

FIG. 11D is a timing diagram illustrating a subsample scan cycle, according to one illustrated embodiment.

Figure 12:
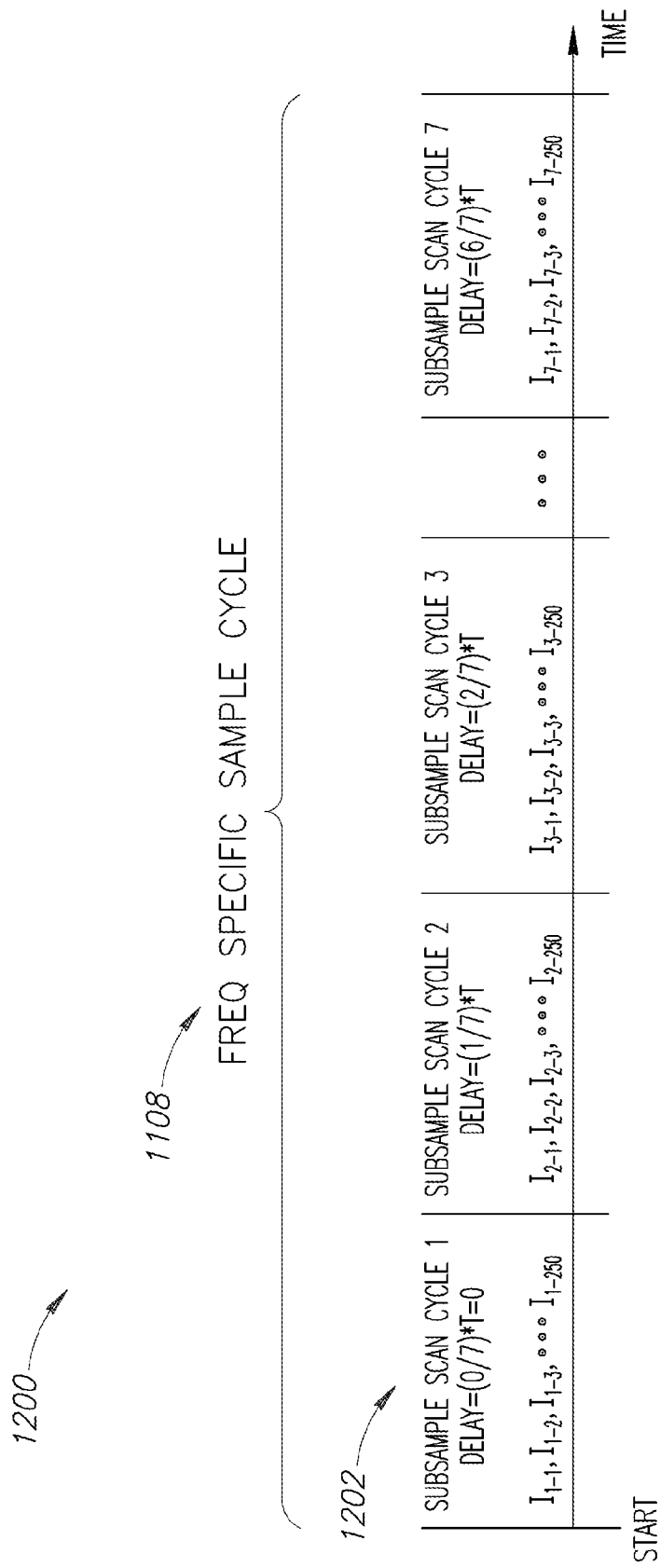

FIG. 12 is a timing diagram illustrating timing for obtaining subsamples utilizing subsample scan cycles, according to one illustrated embodiment.

Figure 13:
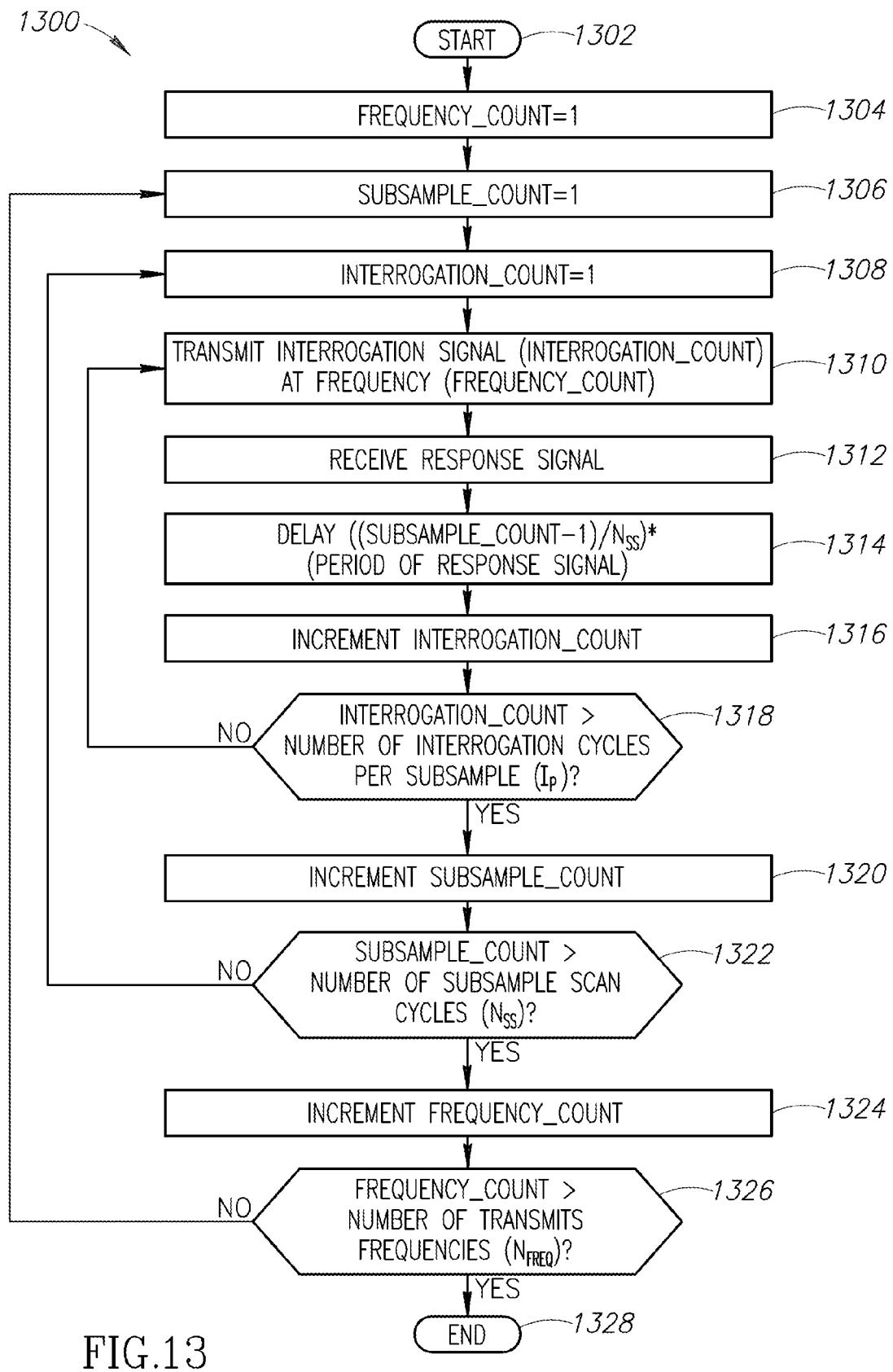

FIG. 13 is a flow diagram showing a process for a scanning method, according to one illustrated embodiment.

Figure 14:
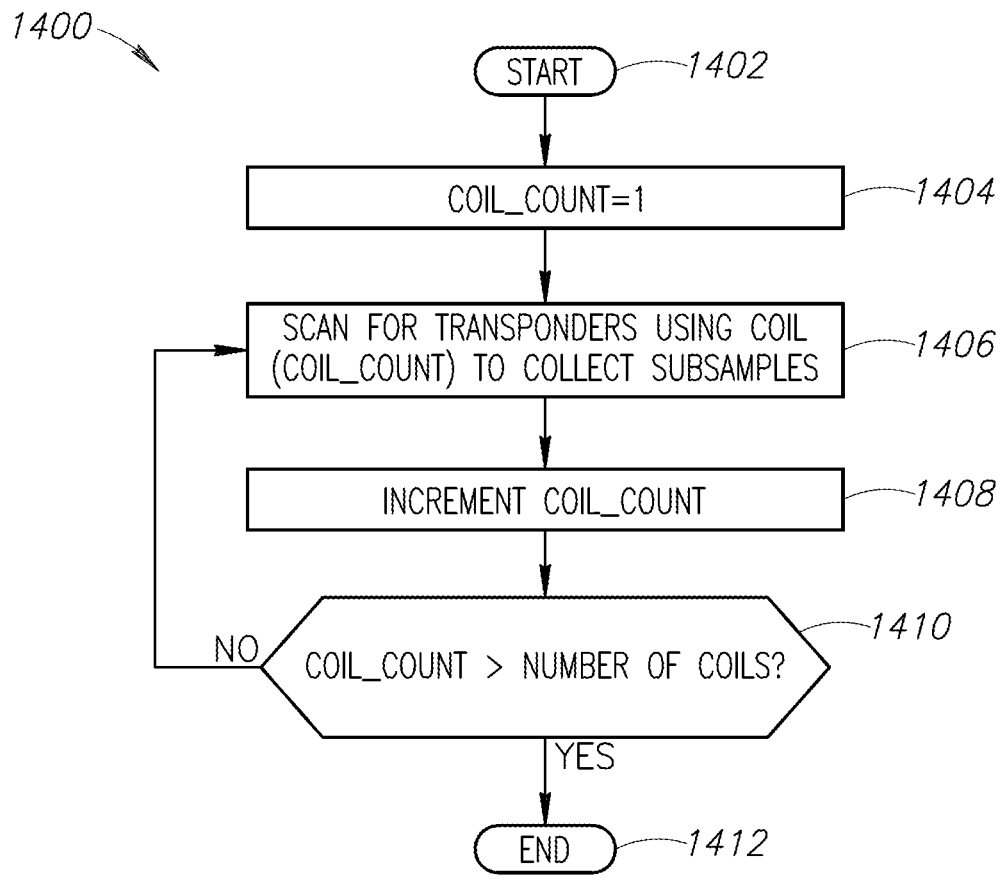

FIG. 14 is a flow diagram showing a process for a scanning method used with multiple coils, according to one illustrated embodiment.

Figure 15:
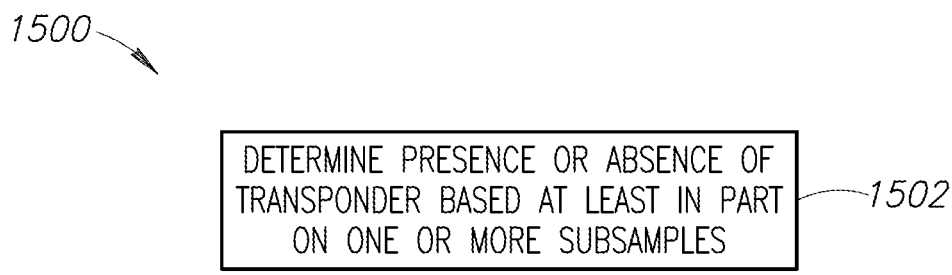

FIG. 15 is a flow diagram showing a method of determining the presence or absence of a transponder by evaluating one or more subsamples, according to one illustrated embodiment.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with transmitters, receivers, or transceivers have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Figure 1:
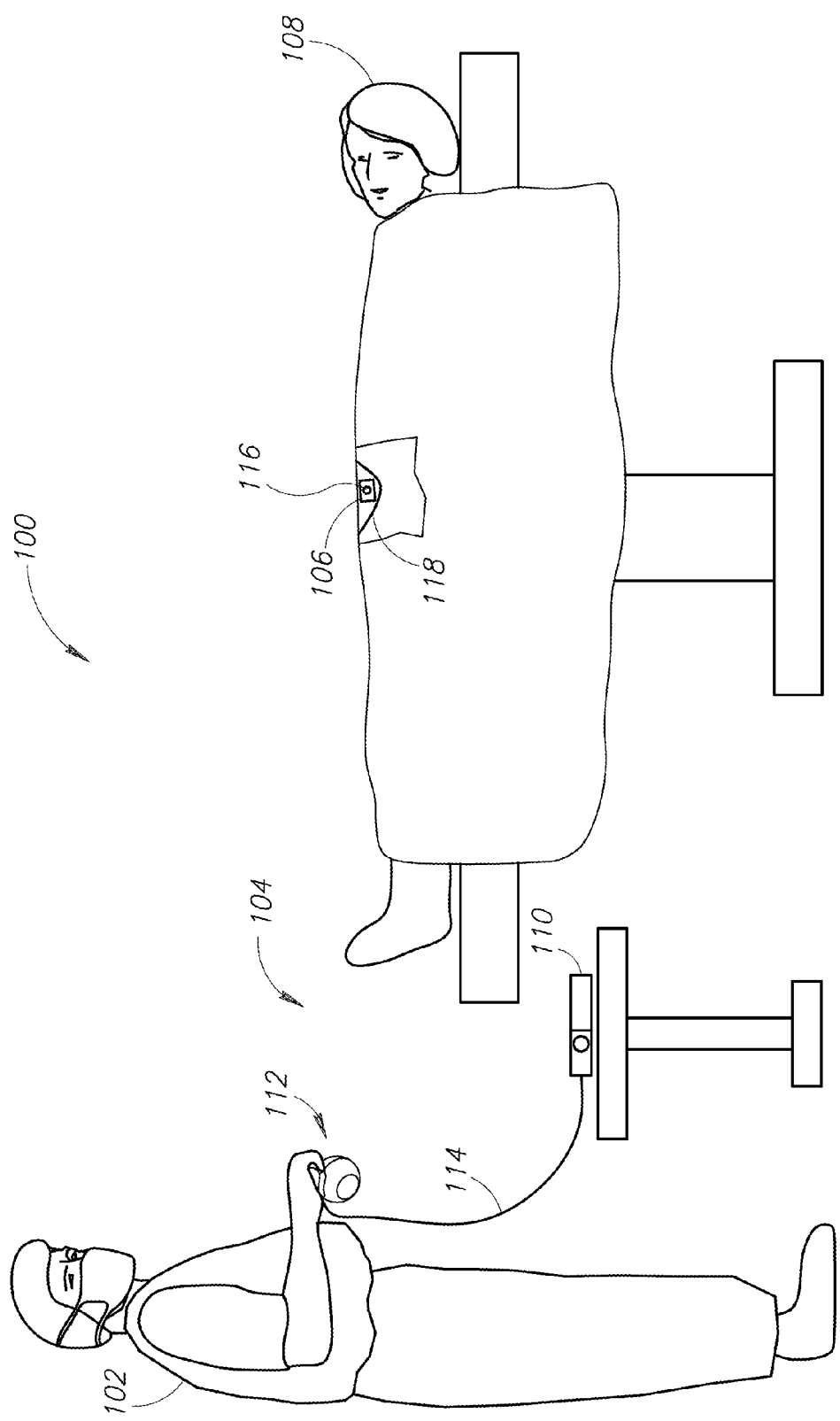
FIG. 1 is a schematic diagram showing a surgical environment illustrating a medical provider using an interrogation and detection system to detect an object tagged with a transponder in a patient, according to one illustrated embodiment.

FIG. 1 shows a surgical environment 100 in which a medical provider 102 operates an interrogation and detection system 104 to ascertain the presence or absence of objects 106 in, or on, a patient 108. The interrogation and detection system 104 may include a controller 110, and one or more antennas 306 (see FIG. 3B) coupled to the controller 110 by one or more communication paths, for example coaxial cable 114. The antennas may be housed within a hand-held probe 112 that may include one or more antenna coils, for example.

The object 106 may take a variety of forms, for example instruments, accessories and/or disposable objects useful in performing surgical procedures. For instance, the object 106 may take the form of scalpels, scissors, forceps, hemostats, and/or clamps. Also for example, the objects 106 may take the form of surgical sponges, gauze and/or padding. The object 106 is tagged, carrying, attached or otherwise coupled to a transponder 116. Embodiments of the interrogation and detection system 104 disclosed herein are particularly suited to operate with transponders 116 which are not accurately tuned to a chosen or selected resonant frequency. Consequently, the transponders 116 do not require high manufacturing tolerances or expensive materials, and thus may be inexpensive to manufacture.

In use, the medical provider 102 may position the probe 112 proximate the patient 108 in a fixed position in order to detect the presence or absence of the transponder 116 and hence an object 106. The medical provider 102 may in some embodiments move the probe 112 along and/or across the body of the patient 108. In some embodiments, the probe 112 may be sized to fit at least partially in a body cavity 118 of the patient 108.

Figure 2A:
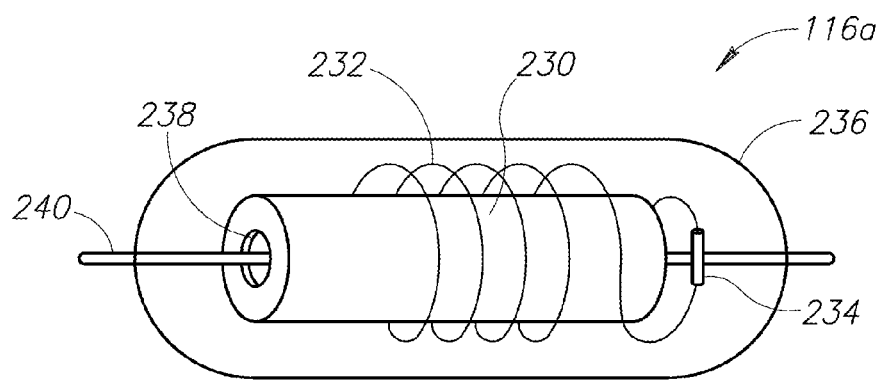
FIG. 2A is a schematic diagram of a transponder, according to one illustrated embodiment.

FIG. 2A shows a transponder 116a according to one illustrated embodiment.

The transponder 116a includes a miniature ferrite rod 230 with a conductive coil 232 wrapped about an exterior surface thereof to form an inductor (L), and a capacitor (C) 234 coupled to the conductive coil 232 to form a series LC circuit. The conductive coil 232 may, for example, take the form of a spiral wound conductive wire with an electrically insulative sheath or sleeve. The transponder 116a may include an encapsulant 236 that encapsulates the ferrite rod 230, conductive coil 232, and capacitor 234. The encapsulant 236 may be a bio-inert plastic that protects the ferrite rod 230, conductive coil 232 and/or capacitor 234 from pressure and/or from fluids, for example bodily fluids.

In some embodiments, the ferrite rod 230 may include a passage 238 sized to receive a physical coupler, for example a bonding tie or string 240. The bonding tie or string 240 may take the form of an elastomeric x-ray opaque flexible elongated member, that may be used to attach the transponder 116a to various types of objects 106, for example surgical sponges. The transponder 116a may have a length of about 8 millimeters and a diameter of about 2 millimeters. Employing such small dimensions ensures that the transponder 116a does not impede deformation of objects 106 such as sponges. The transponder 116a may include an optional diode (not shown), to protect against over-voltage occurrences caused by other electronic instruments.

Figure 2B:
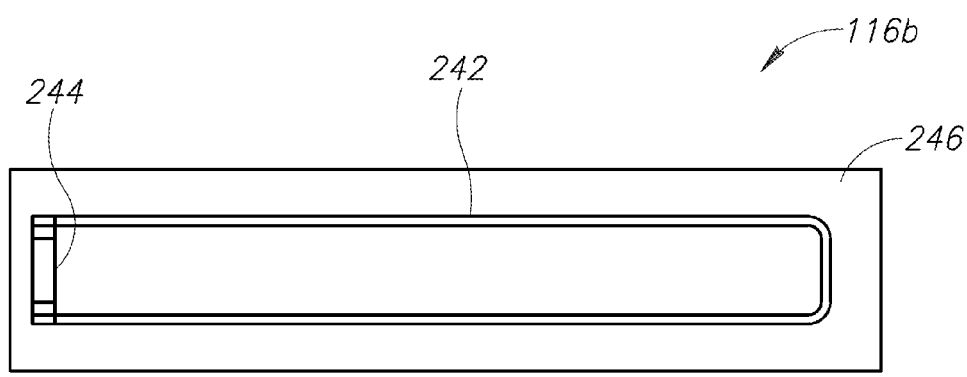
FIG. 2B is a schematic diagram of a transponder, according to another illustrated embodiment.

FIG. 2B shows a transponder 116b, according to another illustrated embodiment.

The transponder 116b includes a single loop of conductive material 242, for example a loop of conductive wire forming an inductor (L), coupled in series to a capacitor 244 (C) to form an LC series circuit. The loop of conductive material 242 and capacitor 244 may be encapsulated in an elastomeric coating or sleeve 246. The dimensions of the transponder 116b may be similar to the dimensions of the transponder 116a. In some embodiments, the dimensions of the transponder 116b are greater than the dimensions of the transponder 116a. The transponder 116b is highly flexible, and thus may provide its own thread-like or string-like attachment to various types of objects 106.

Figure 2C:
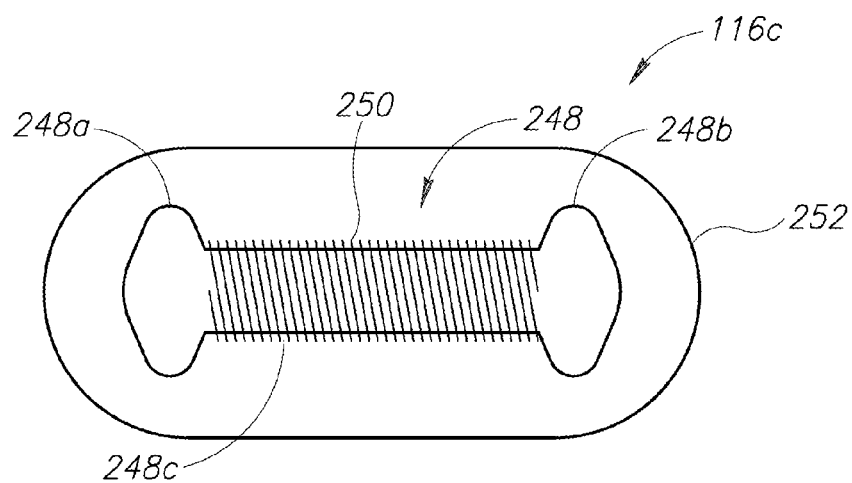
FIG. 2C is a schematic diagram of a transponder, according to a further illustrated embodiment.
Figure 2D:
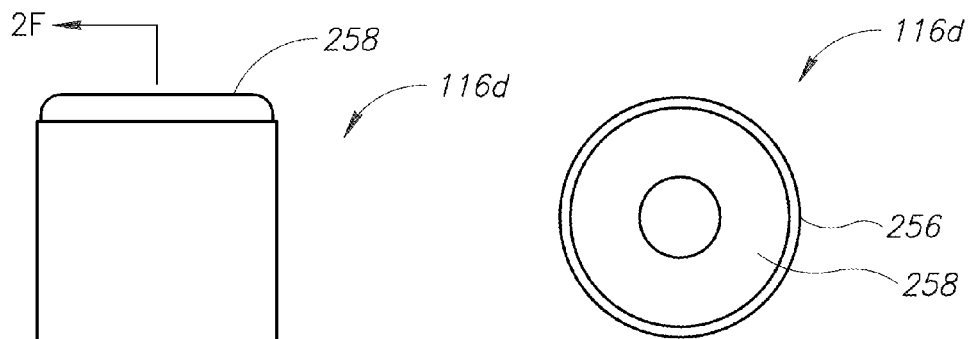
FIG. 2D is a side elevational view of a transponder, according to yet a further illustrated embodiment.
Figure 2E:
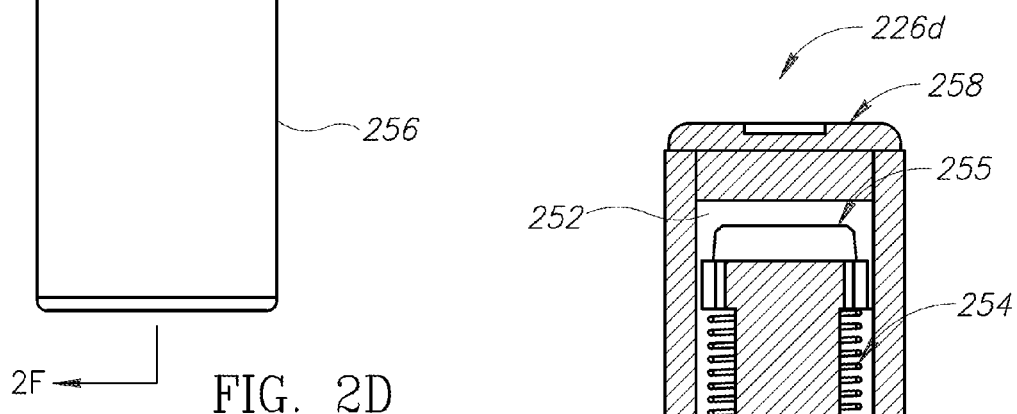
FIG. 2E is an end view of the transponder of FIG. 2D.
Figure 2F:
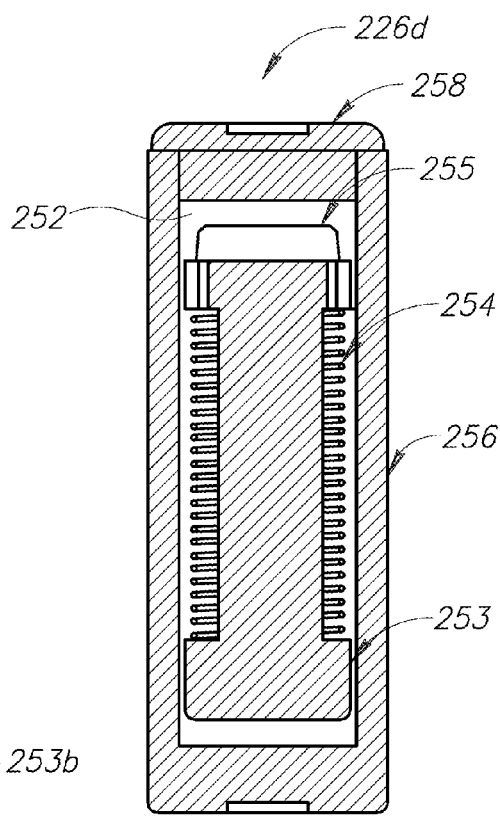
FIG. 2F is a cross-sectional view of the transponder of FIG. 2D, taken along section line 2F.
Figure 2G:
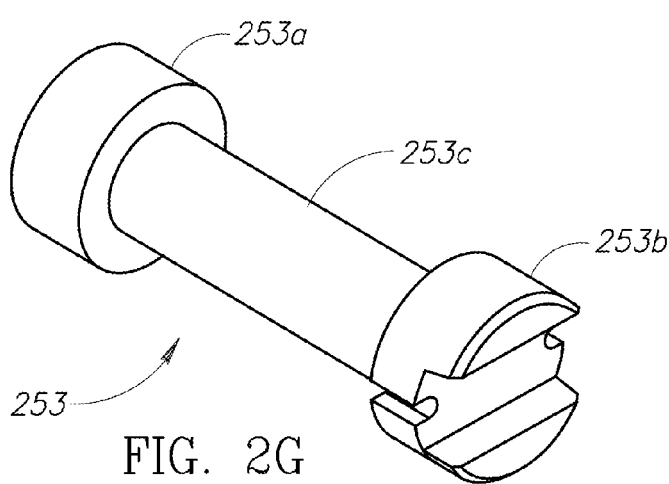
FIG. 2G is an isometric view of a ferrite core of the transponder of FIG. 2D.

FIG. 2C shows a transponder 116c according to a further embodiment.

The transponder 116c includes a dumbbell-shaped ferrite rod 248 having broad end portions 248a, 248b, and a narrow intermediate portion 248c which is wrapped by a conductive coil 250. The broad end portions 248a, 248b contain the conductive coils 250. Such a design may provide stronger and/or more reliable signal emission than transponders 116a, 116b fashioned with cylindrical ferrite rods. The transponder 116c may optionally include an encapsulant 252. Further details regarding the transponder 116c may be found in U.S. Provisional Patent Application No. 60/811,376 filed Jun. 6, 2006. In some embodiments, the transponder 116c may be formed as a fusiform-shaped object, with truncated ends. The fusiform shape may be advantageous over cylindrical shaped transponders 116a, 116b in reducing the likelihood of close parallel alignment of the transponders 116a, 116b, which may produce transponder-to-transponder interaction and interference.

FIGS. 2D-2G show a transponder 116d according to yet a further embodiment.

The transponder 116d includes a ferrite core 253, inductor (L) 254, and capacitor (C) 255 electrically coupled to the inductor 254 to form an LC series circuit. The transponder 116d also includes a capsule 256 with a cavity 257 open at one end to receive the ferrite core 253, inductor 254 and capacitor 255, as well as a lid 258 to close the open end of the capsule 256.

The ferrite core 253 may, for example, take the form of a soft ferrite drum, and may, for example, be formed of Nickel Zinc. Suitable ferrite cores 253 may be commercially available from TAK FERRITE as part no. L8A DR3X9 B=1.8 F=6 or from HUAH YOW under part no. 10R030090-775. The drum may have a pair of larger diameter end portions 253a, 253b, with a smaller diameter intermediate portion 253c therebetween.

The inductor 254 may take the form of magnet wire wrapped around the intermediate portion 253c of the ferrite core 253. The magnet wire may, for example, have a dimension of approximately 41 American Wire Gauge (AWG), although some embodiments may employ wires or conductors of larger or small gauges. Suitable inductors 254 may be commercially available from ELEKTISOLA under part no. PN-155 or from ROSEN under part no. 2UEW-F. The inductor may, for example, include approximately 432 turns, over approximately 6.5 layers, although some embodiments may include a greater or lesser number of turns and/or layers. The transponder 116d may include tape and/or epoxy enveloping the inductor 254. Suitable tape may be commercially available from 3M under part nos. 1298, 1350-1 or PLEO 1P801, while suitable epoxy may be commercially available from LOCKTITE under part no. 3211.

The capacitor 255 may, for example, take the form of a ceramic capacitor. The capacitor 255 may, for example, have a capacitance of 470PF, 100V, with a Quality factor of Q>2200 @ 1 MHz. Suitable capacitors 255 may be commercially available from SANJV DIELECTRIC under part no. 0805NPO471J101 or from FENG HUA under part no. 0805CG471J101NT.

The capsule 256 and lid 258 may, for example, be formed of a polypropylene. Suitable capsules 256 and lids 258 may be commercially available from WEITHE ELECTRON (HK) COMPANY, under part specification CASE 4.3×12.6. The combination of the capsule 256 and lid 258 may, for example, have a length of approximately 12.8 mm and a diameter of 4.4 mm. Circuit bonds may, for example, employ UNITED RESINS CORP. part no. 63001500 CIRCUIT BOND LV, while solder may take the form of a lead free 96.5% Ag/3% Sn/0.5 Cu solder.

The transponders 116 may be attached to hemostats, scissors, certain forms of forceps, and the like. In some embodiments, the transponders 116 may be coupled to the object 106 by way of a clamp or holder. In some embodiments, the transponders 116 may be retained within a cavity of the holder. In some embodiments, the holder may be fashioned of a durable deformable material, such as surgical grade polymer, which may be deformed to clamp securely onto the finger or thumbhole of an instrument. In other embodiments, the transponders 116 may be attached to objects 106 by way of pouches fashioned of sheet material (e.g., surgical fabric) surrounding the transponder 116. The transponder 116 is retained within the pouch, and in some embodiments the pouch may be sewn or otherwise sealed. Sealing may be done with adhesive, hot glue, clamping, grommeting, or the like.

Figure 3A:
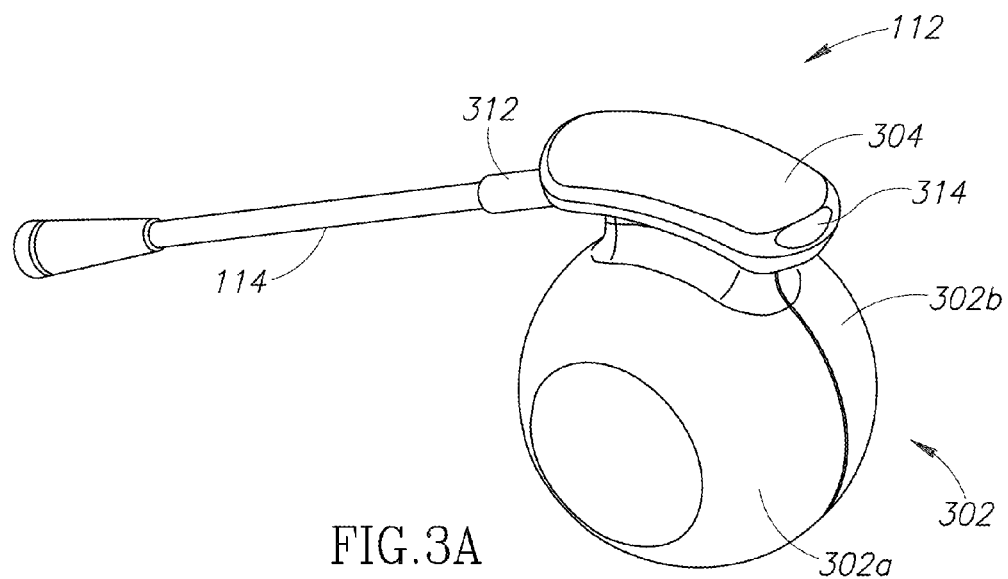
FIG. 3A is an isometric view of a probe of the interrogation and detection system, according to one illustrated embodiment.
Figure 3B:
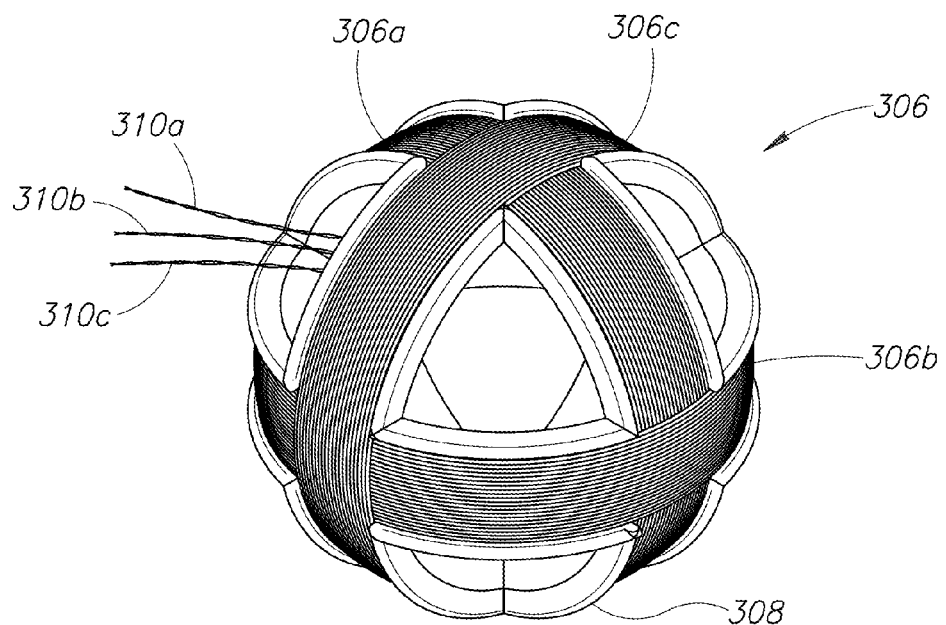
FIG. 3B is an isometric view of a coil form and three mutually orthogonal coils of the probe of FIG. 3A.

FIGS. 3A and 3B show the probe 112 also illustrated in FIG. 1, according to one illustrated embodiment.

The probe 112 may include a first body portion structure 302a and a second body portion structure 302b that mates to the first body portion structure 302a to form a substantially spherical body portion 302. The probe 112 may include a handle portion 304 extending from the spherical body portion 302. The handle portion may be sized and dimensioned to be gripped by the hand of a medical provider 102 (FIG. 1). In some embodiments, the body portions 302a, 302b may be identical in shape to one another.

The body portion 302 may define one or more cavities sized and dimensioned to receive an antenna 306 (FIG. 3B). The antenna 306 may, for example, take the form of an annulus or air-coil formed of coils of conductive material, for example wire. In one embodiment, the antenna 306 includes 10 turns evenly spaced between an inner diameter of about 11 inches and an outer diameter of about 14 inches. The antenna 306 acts as an inductor.

As shown in FIG. 3B, the antenna 306 or plurality of antennas may include three antenna coils 306a, 306b, and 306c mutually orthogonal to each other. In the illustrated embodiment, the antenna coils 306a, 306b, and 306c are wound around a coil form or bobbin 308. Electrical wires 310a, 310b, and 310c, of the respective coils 306a, 306b, and 306c may be electrically coupled to the controller 110 via the cable 114.

In some embodiments, the antenna 306 may be formed as a set of coils in the form of the hand-held probe 112 and/or may be embedded in a mat or other object. For example, the antenna 306 may be embedded in a mat that is detachably secured to a patient support structure. Examples of such antennas are disclosed in in U.S. patent application Ser. No. 13/422,192, filed Mar. 16, 2012, which is incorporated by reference herein it its entirety.

In some embodiments the antenna 306 may include six antenna coils, or a greater or fewer number of antenna coils. For example, fewer antennas 306 may be employed for use in childbirth or delivery, as compared to environments employing standard operating room tables. For example, the antennas 306 may be arranged in sets, or may be aligned in linear, two-dimensional, or three-dimensional arrays. Also for example, some antennas 306 may be staggered with respect to other ones of the antennas 306. Also for example, some antennas 306 may overlie other ones of the antennas 306, for example being carried on separate faces or layers of a substrate or sheet. At least some of these arrangements of antennas 306 may be operated as a phased antenna array. The antennas 306 may take forms other than coils, for example dipole or slot antennas, to name only a few.

The probe 112 may include a coupling member 312 which may be positioned in the cavity in the handle portion 304 to provide a connector to communicatively couple to an end of the coaxial cable 114 to the antenna 306. The coupling member 312 may take the form of a standard coaxial connector. Some embodiments may employ other types of communications pathways between the controller 110 and the antenna 306, and thus may employ other types of coupling members or connectors.

In some embodiments, the probe 112 may include one or more user interface devices, for example one or more visual indicators 314 (FIG. 3A) to provide visual indications to the medical provider 102. Such may, for example, take the form of one or more light emitting diodes, which may produce one or more different colors. Such user interface devices may additionally or alternatively include a speaker or other transducer, operable to produce a sound or other sensory indication, for example a tactile sensation. Such user interface devices may be configured to provide sensory feedback to the medical provider 102 indicative of an operating condition of the interrogation and detection system 104. For example, such may indicate when the interrogation and detection system 104 is operating, when the presence of a transponder 116 has been identified, and/or when an error has occurred. Locating user interface devices on the probe 112 may be advantageous since the medical provider 102 will typically focus their attention on the probe 112 while scanning the patient 108.

Figure 4:
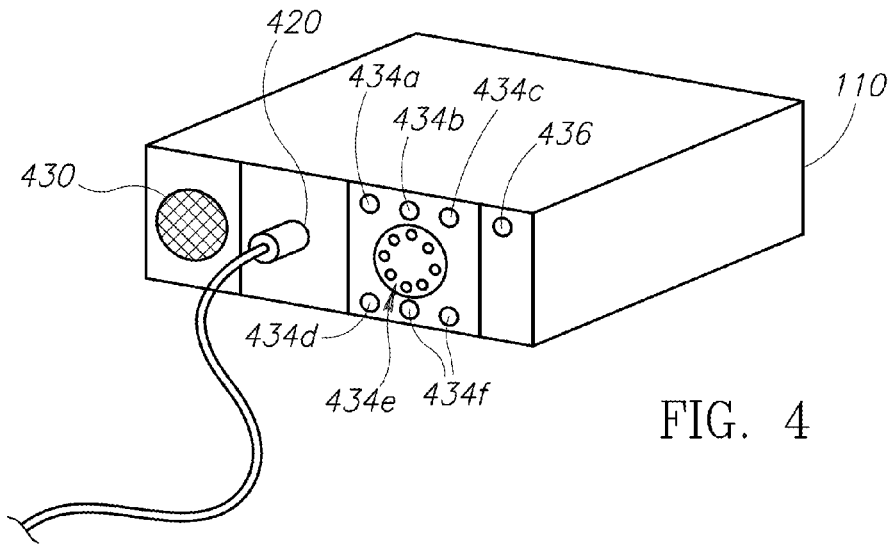
FIG. 4 is an isometric view of a controller of the interrogation and detection system, according to one illustrated embodiment.

FIG. 4 shows the controller 110 according to one illustrated embodiment. The controller 110 includes an input port 420 with an appropriate coupling member, for example a connector to allow an end of the coaxial cable 114 to be communicatively coupled to the controller 110. As noted above, some embodiments may employ other communications pathways between the controller 110 and the antenna 306, hence other types of coupling members or connectors may be employed. The controller 110 may also include a power switch (not illustrated in FIG. 4), for example, positioned on a back or rear of the controller 110. The controller 110 may further include a power cord (not shown) to couple the controller 110 to a suitable power supply. The power supply may, for example take the form of a standard wall outlet or any other power supply or source. The controller 110 may further include one or more user interface devices for providing information to a user. For example, the controller 110 may include one or more visual indicators, for instance one or more light emitting diodes (LEDs) 434a-f and/or liquid crystal displays. Additionally, or alternatively, the controller 110 may include one or more speakers 430 or other transducers operable to produce sound or tactile sensations. The controller 110 forms a transmitter and receiver, or transceiver, to transmit interrogation signals and receive responses to those signals, as well as to receive electromagnetic signals which may be indicative of noise.

Figure 5:
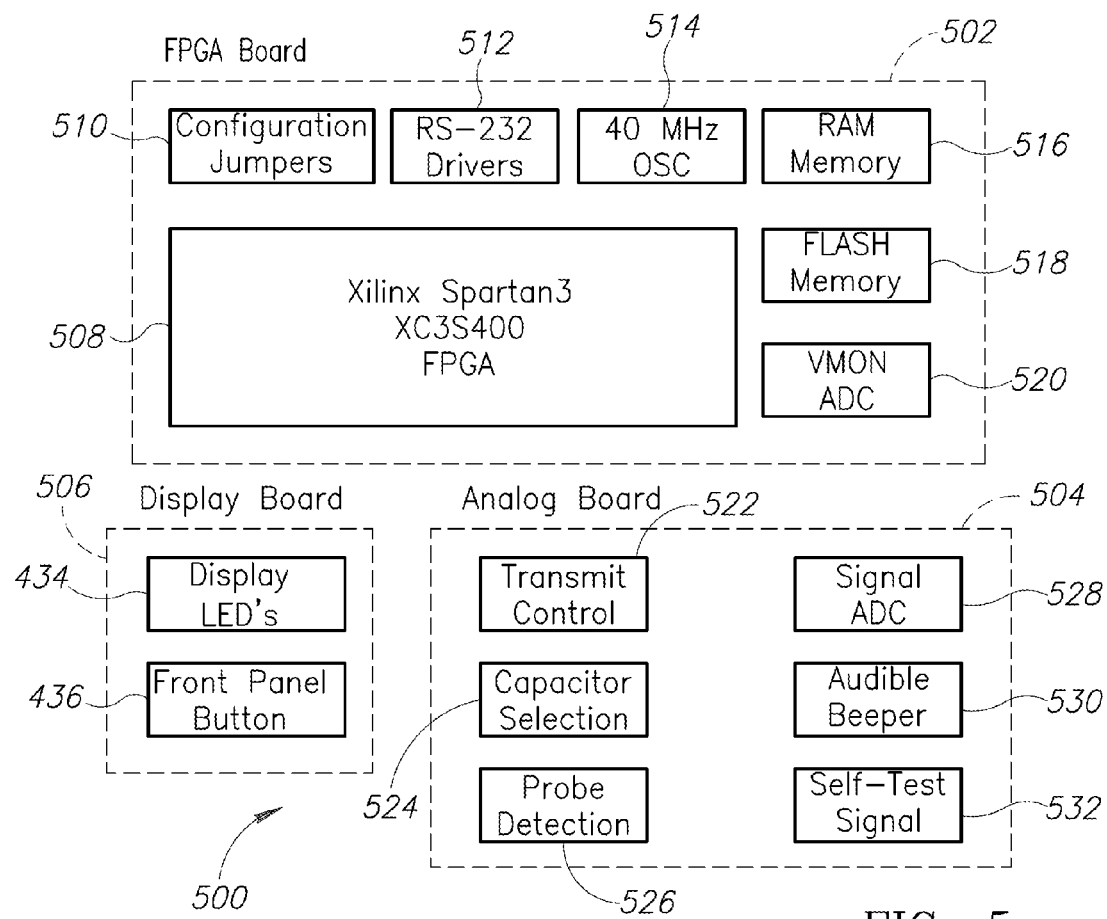
FIG. 5 is a schematic diagram of a control system of the interrogation and detection system, according to one illustrated embodiment.

FIG. 5 shows a control system 500 of the interrogation and detection system 104, according to one illustrated embodiment.

The control system 500 includes a field programmable gate array (FPGA) board 502, analog board 504 and display board 506, communicatively coupled to one another.

The FPGA board includes an FPGA 508, configuration jumpers 510, RS-232 drivers 512, oscillator 514, random access memory (RAM) 516, flash memory 518, and voltage monitoring (VMON) analog-to-digital converter (ADC) 520. The FPGA 508 may take the form of a Xilinx Spartan3 FPGA, which runs FPGA and application software. As explained below, on power up, the FPGA reads the configuration information and application software program from the flash memory 518.

The configuration jumpers 510 are used to select the application software configuration.

The RS-232 drivers 512 are used to allow the application software to communicate using serial RS-232 data for factory test and diagnostics.

The oscillator 514 sets the clock frequency for the operation of the FPGA 508. The oscillator 514 may, for example, take the form of 40 MHz oscillator, although other frequencies are possible.

The RAM 516 is connected to the FPGA 508 and is available for use by the application software. The application software uses this memory space for storage of both the executable program and program data. The RAM 516 may, for example, have a capacity of 1 MB.

The flash memory 518 contains both the FPGA configuration data and the binary application program. On power up the FPGA 508 reads the flash memory to configure the FPGA 508 and to copy the application program binary data from the flash memory 518 to the RAM 516.

The voltage monitor ADC 520 is connected to the FPGA 508 and controlled by the application software to monitor a power supply and regulated voltage forms in controller electronics.

The analog board 504 includes transmit control circuits 522, capacitor selection circuits 524, probe detection circuit 526, signal ADC 528, audible beeper 430 and self-test signal 532.

The transmit control circuits 522 on the analog board 504 are controlled by signals from the FPGA 508 to generate a transmit waveform.

Optional capacitor selection circuits 524 on the analog board 504 are controlled by the signals from the FPGA 508 to tune the drive circuit to match an inductance of the antenna 306.

The probe detection circuit 526 detects when a probe 112 is connected to the controller 110. The output of the probe detection circuit 526 drives a signal denominated as the LOOP_LEVEL_OUT signal, which is an input to the FPGA 508.

The signal ADC 528 is used as a receiver to sample the signals received at the antenna 306 from the transponders 116 (FIGS. 2A-2C). The signal ADC 528 may, for example, operate at a 1 MHz sample rate and may have 12-bits of resolution. The FPGA board 502 generates the timing and control signals for the signal ADC 528, which signals are denominated as ADC_CTRL, CS1, SCLK, and SD0.

The audible speaker or beeper 430 can be controlled by the FPGA 508 to emit sounds to indicate various states, modes or operating conditions to the medical provider 102 (FIG. 1).

The FPGA 508 can cause the generation of the self test signal 532 on the analog board 504 at the signal ADC 528. Self-testing may be performed at start up, and/or at other times, for example periodically or in response to the occurrence of certain conditions or exceptions.

The display board 506 includes user interface elements, for example a number of light emitting diodes (LEDs) 434. The FPGA board 502 can control the LEDs 434 on the display board 506. The display board 506 also includes a user selectable activation switch, denominated as front panel button 436. The front panel button 436 is connected to the display board 506 which allow the FPGA 508 to monitor when the front panel button 436 is activated (e.g., pressed).

Figure 6:
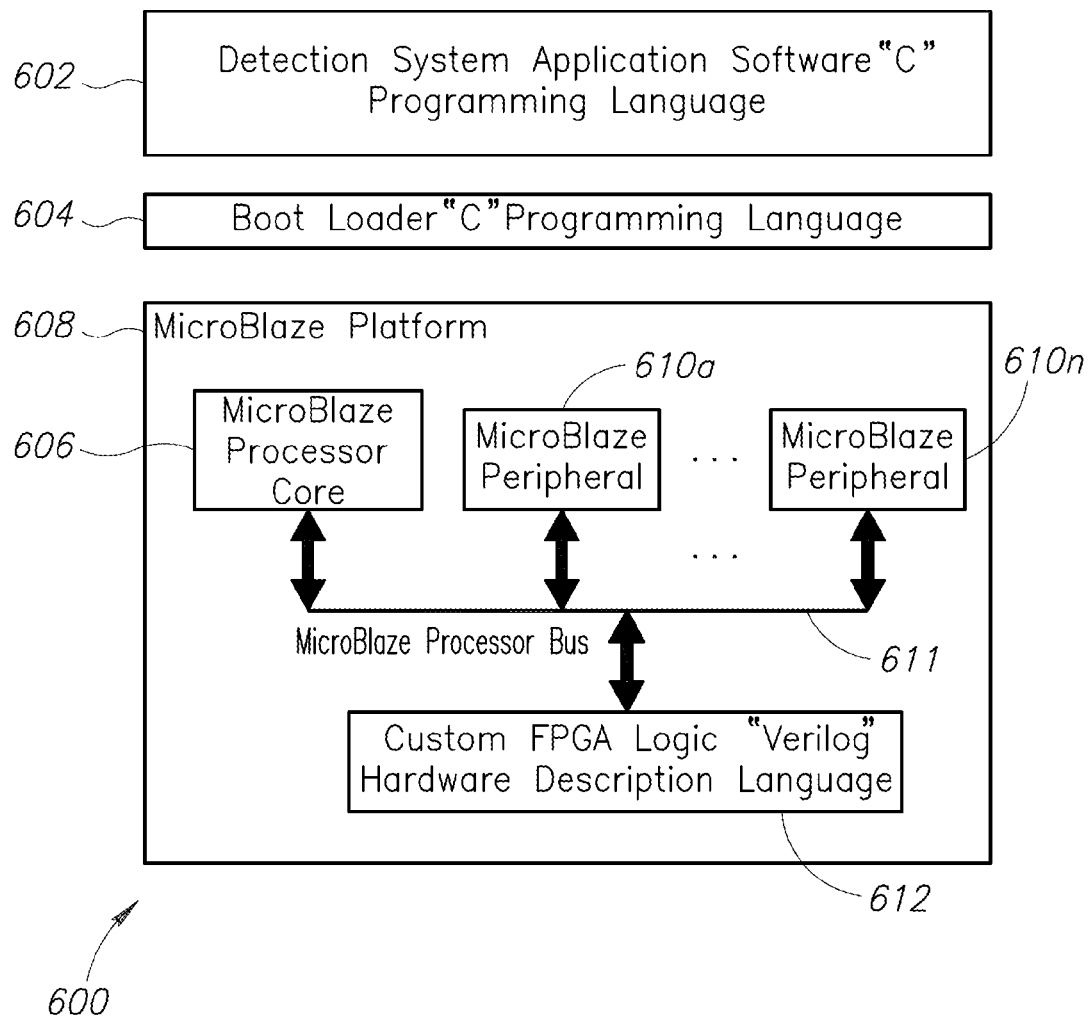
FIG. 6 is a schematic diagram of a software configuration of the interrogation and detection system, according to one illustrated embodiment.

FIG. 6 shows a software configuration 600 of the interrogation and detection system 104, according to one illustrated embodiment.

The software may include application software 602 that is responsible for operating the controller 110 (FIGS. 1 and 4). The application software 602 controls the timing for generating transmit pulses, processes sampled data to detect transponders 116 (FIGS. 2A-2C), and indicates status to the user with the display LED's 434 (FIG. 5) on the display board 506 and/or via the audible speaker or beeper 130 on the analog board 504. The application software 602 is stored in the flash memory 518 (FIG. 5) and transferred into the RAM 516 by a boot loader 604.

The boot loader 604 is automatically loaded when the FPGA 508 is configured, and starts execution after a processor core 606 is reset. The boot loader 604 is responsible for transferring the application software 602 from the flash memory 518 to the external RAM 516.

The processor platform 608 is configured into the FPGA 508 (FIG. 5) on power up from the configuration information stored in the flash memory 518. The processor platform 608 implements a custom microprocessor with a processor core 606, peripherals 610a-610n, and custom logic 612.

The processor core 606 may take the form of a soft processor core supplied by XILINX under the name MICROBLAZE, that implements a 32-bit processor including memory cashes and a floating point unit. A soft core processor is one that is implemented by interconnected FPGA logic cells instead of by a traditional processor logic. The processor core 606 is connected to the internal FPGA peripherals 610a-610n using a 32-bit processor bus 611 called the On-Chip Peripheral Bus. The XILINX supplied peripherals for the MICROBLAZE processor core 606 include external memory interfaces, timers, and general purpose I/O.

The custom logic 612 to create the transmit signals, sample the ADC 128, and accumulate the transponder return signals is designed as a peripheral to the processor core 606. The custom logic 612 is the part of the design of the FPGA 508.

In some embodiments, a detection cycle that employs an approach that optimizes signal to noise ratio (SNR) by a receiver portion may be implemented. Such may, for example, advantageously increase range or increase sensitivity at a given range. One embodiment is optimized based on having an overall detection cycle that performs well for transponders with resonant frequencies from approximately 136 kHz to approximately 154 kHz.

The application software 602 (FIG. 6) implements the detection cycle using transmission or interrogation in a frequency band centered around a center channel or frequency. The application software 602 sequences through a non-measurement portion (i.e., gap), and two distinct measurement portions, denominated as a noise detection portion and an signal measurement portion, each detection cycle. In at least one embodiment, the detection cycle may, for example, be approximately 275 milliseconds, the gap portion may be approximately 10 milliseconds, the noise portion approximately 37 milliseconds and the signal measurement portion approximately 228 milliseconds.

During the noise detection portion, which may, for example be a first measurement portion of each detection cycle, ambient or background noise is measured or sampled, providing a value indicative of a level of ambient or background noise for the particular environment. The noise measurements or are taken or captured at a time sufficiently after excitement of the transponders 116 by the interrogation signal emitted by the transmitter such that the transponders 116 are substantially not resonating or responding to any previous excitation by interrogation signals. In particular, a number N of measurements or samples are taken during the noise detection or first measurement portion.

During the signal measurement portion, which may, for example take the form of the second measurement portion of each detection cycle, responses by transponders 116 are measured or sampled. The response measurements or samples are taken with the transmitter transmitting or at a time sufficiently close to excitement of the transponders 116 by the interrogation signal emitted by the transmitter such that the transponders 116 are still substantially resonating or responding to the interrogation signal. In particular, a number M of measurements or samples are taken during the interrogation or second measurement portion.

While the signal measurement portion may be one contiguous or continuous portion, in some embodiments the signal measurement portion may take the form of two or more separate portions or intervals. Each of the portions may employ the same transmit frequency band, for example centered around 145 kHz. Other center channels or frequencies may for example be 136 kHz, 139 kHz, 142 kHz, 145 kHz, 148 kHz, 151 kHz and/or 154 kHz, or any other frequency suitable for exciting the transponder to resonate. Some embodiments may employ frequency hopping, for example transmitting a different center channel or frequency for each of a plurality of signal measurement portions of each detection cycle. Such is discussed further in U.S. provisional patent application Ser. No. 60/892,208, filed Feb. 28, 2007 and U.S. non-provisional application Ser. No. 11/743,104, filed May 1, 2007.

The gap portion may provide time for the response of the transponders 116 to the interrogation signal to decay sufficiently to allow measurement of noise.

Some embodiments may arrange the gap, the noise detection portion and/or the signal measurement portion, or parts thereof, in a different order.

In one embodiment, the time to accumulate the noise sample or value indicative of a noise level may, for example, be approximately 37 milliseconds, and the time to accumulate the transponder signal measurement approximately 228 milliseconds. Along with a gap of approximately 10 milliseconds between the signal and noise portions, the time for a single detection cycle would be approximately 275 milliseconds. As noted above, the transmitter is OFF during the noise measurement portion of each detection cycle to allow the receiver to measure ambient noise, and the signal detection portion is taken with the transmitter transmitting a wideband interrogation signal about the particular center channel or frequency.

The noise samples collected by the receiver may be accumulated and a highest one or more of multiple samples or measurements over one or more detection cycles selected or used to prevent unwarranted fluctuations. The response signals from the transponder 116 may be accumulated and/or averaged or integrated over one detection cycle or over multiple detection cycles.

The number N of noise measurements or samples and/or the number M of response signal measurements or samples may be selected to achieve a desired ratio of N to M, in order to achieve or maintain a desired signal to noise ratio. For example, obtaining 200 noise measurements or samples and 800 response measurements or samples each detection cycle results in an SNR of approximately 2 (e.g., the square root of the 800 divided by 200). While an SNR as low as 1.1:1 may be sufficient in some embodiments, an SNR approaching 2:1 ensures sufficient differentiation to eliminate or reduce the possibility of false positives to an acceptable level for the particular applications envisioned herein. Any known hardware and software accumulators, summer, integrators and/or other hardware or software may be suitable.

The accumulated or integrated received signal may be matched filtered with both in-phase and quadrature reference signals to determine the signal magnitude. The received receive signal is matched filtered with a plurality of reference signals, for example with the seven reference signals, for instance as shown in Table 1 below. Some embodiments may employ matched filtering before accumulating or integrating the received signal.

TABLE 1

| Match Frequency |
| --- |
| 136 kHz |
| 139 kHz |
| 142 kHz |
| 145 kHz |
| 148 kHz |
| 151 kHz |
| 154 kHz |

The maximum value for the matched filters (e.g., seven matched filters) with active transmit may be compared with an adjusted detection threshold. If the maximum value is greater than the detection threshold, then a response signal from a transponder 116 may be considered as having been detected, and appropriate action is taken, such as discussed below with reference to FIG. 7. Alternatively or additionally, the interrogation and detection system may employ a fast Fourier transform approach in lieu of matched filtering.

The noise filtering processes the measured or sampled noise values for each detection cycle to determine a stable noise floor value. The output of the noise filter may, for example, be the maximum of either the current noise measurement or a decayed value of the previous noise floor.

The output of the noise filter may be an estimate of the current noise floor level after selecting the highest of a plurality (e.g., 6) of noise measurements or samples. The filtered noise floor may advantageously include samples collected, captured or measured both before and after a given signal sample is collected, captured or measured. Thus, for any sample of a given detection cycle the noise floor may include noise samples from the given detection cycle, as well as a next successive detection cycle. The filtered noise floor may additionally, or alternatively, include noise samples from one or more successively preceding detection cycles, as well as one or more successfully succeeding detection cycles.

Figure 7:
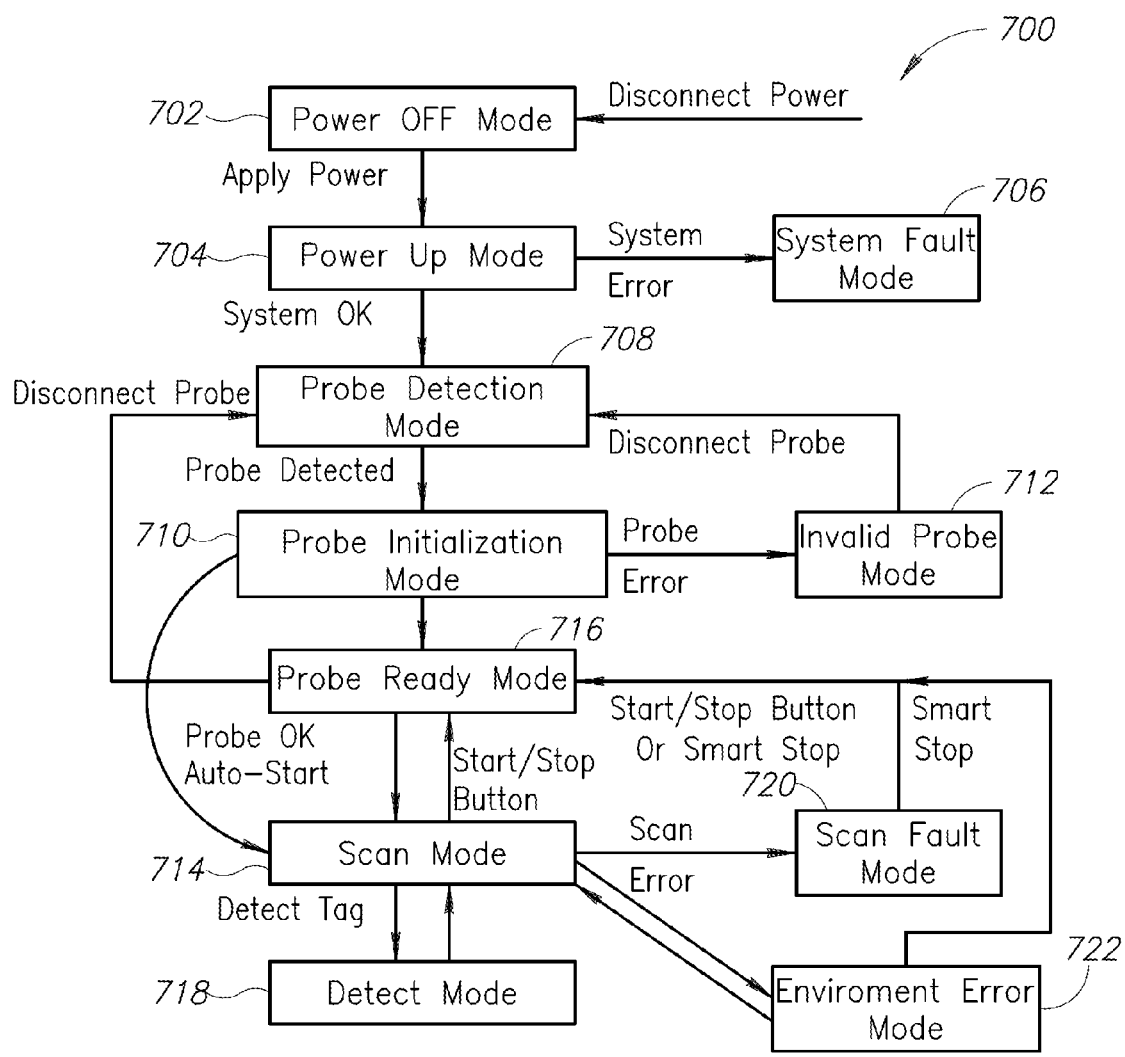
FIG. 7 is a flow diagram of a method of operating an interrogation and control system, according to one illustrated embodiment.

FIG. 7 shows a method 700 of operating the interrogation and detection system 104 according to one illustrated embodiment.

In response to detecting a disconnect of power, the interrogation and detection system 104 enters a Power OFF mode at 702. For example, the Power OFF mode 702 may be entered when the controller 110 (FIGS. 1 and 4) is unplugged or when the power switch on the controller 110 is turned OFF. In the Power OFF mode 702, the Power LED 434*a* and other front panel LEDs 434 will be turned OFF (non-emitting). The software 200 is inoperative in the Power OFF mode 702.

In response to detecting an application of power, the interrogation and detection system 104 enters a Power-Up mode 704. The Power UP mode 704 may, for example, in response to the application of power to the controller 110 and turning ON the switch on the back of the controller. In the Power-Up mode 704, a Power LED 434*a* may be turned ON or illuminated, and may remain ON or illuminated as long as the power is applied and the switch is in the ON state. In response to entering the Power UP mode 704, the software 200 will perform software initialization, built in tests, and an audio/visual test.

If a fault is detected, the software 200 progresses to a System Fault Mode 706. If no faults are detected, the software 200 may turn a System Ready LED green, and enter a Probe Detection Mode 708.

In the System Fault Mode 706, the software 200 may cause an indication of the detection of a system fault by blinking a System Ready LED 434*b* yellow, and/or issuing a sequence of rapid beeps or other sounds. The corrective action for the System Fault Mode 706 is to cycle power to reinitiate the Power Up mode 704. Continued failure indicates a failed controller 110.

In the Probe Detection Mode 708, the software 200 checks for a probe 112 connected to the controller 110. The Probe Detection Mode 708 may be indicated by turning the System Ready LED 434*b* green and turning the Probe Ready LED 434*c* OFF. If no probe 112 is detected, the software 200 remains in the Probe Detection Mode. If a probe 112 is detected, the software 200 progresses to the Probe Initialization Mode 710.

At the start of the Probe Initialization Mode 710, after the detection of a probe 112, the software 200 may turn the Probe Ready LED 434*c* yellow and check for the presence of a fuse in the probe 112. If a fuse is found, the software 200 may attempt to blow the fuse and verify that the fuse was correctly blown. After the fuse is blown the software 200 may verify that probe 112 is operating within tolerances. The software 200 may indicate that the probe 112 is ready by turning the Probe Ready LED 434*c* green. The software 200 may also start a timer which will allow the probe 112 to be disconnected and reconnected to the controller for a period to time (e.g., 5 hours) after the fuse is blown.

The controller 110 may determine the adjustments or fine tuning to be made about the center frequencies or channels during Probe Initialization Mode 710. In particular, the controller 110 may determine the particular frequency in each of the frequency bands that elicits the response with the highest voltage. The controller may determine such by varying the capacitance of the LC circuit using the switched capacitors C33-C36 during the Probe Initialization Mode 710. The particular combination of switched capacitors C33-C36 which achieved the response with the highest voltage may then be automatically employed during a Scan Mode 714 (discussed below) to adjust or fine tune about the center frequency or channel in each broad band of transmission. Other approaches to determining the fine tuning may be employed.

If the software 200 does not successfully complete the Probe Initialization Mode 710, the software 200 enters an Invalid Probe Mode 712. If the software 200 successfully completes the Probe Initialization Mode 710, the software 200 progresses to the Scan Mode 714 to automatically start scanning.

In the Invalid Probe Mode 712, the software 200 may blink the Probe Ready LED 434*c* yellow and issues a slow beep pattern.

The Invalid Probe Mode may be entered in response to any of the following conditions:

The probe 112 connected to the controller 110 is out of tolerance.

The controller 110 is unable to blow the fuse in the probe 112.

The probe 112 does not have a fuse and more than the set time period has past (e.g., 5 hours) since a fuse was blown.

The probe 112 does not have a fuse and the controller 110 has been restarted.

The probe 112 has been connected to the controller for more than the set time period (e.g., 5 hours).

The probe 112 is detuned due to close proximity to metal.

The corrective action for the Invalid Probe Mode 712 is to remove the invalid probe 112 and attach a new probe 112 to the controller 110 that contains a fuse or to reconnect the probe 112 while holding it in the air at least 2 feet away from large metallic objects.

The software 200 enters the Scan Mode 714 when the probe 112 is ready and the operator presses a Start/Stop button. The software 200 may issue a short three beep pattern via the speaker or beeper 130 when entering the Scan Mode 714 to identify the entry to the user.

In the Scan Mode 714, the software 200 may continuously or periodically perform the following functions.

Look for response signals from transponders 116
Monitor the noise level
Insure the probe 112 is connected and operating correctly
Blink the LED's in a circular pattern When the operator or user pushes the Start/Stop button or the a scan maximum time interval (e.g., 4 minute) has been reached, the software 200 may issue a short three beep pattern and return to the Probe Ready Mode 716.

When an appropriate response signal from a transponder 116 is detected while in Scan Mode 714, the software 200 may turn ON an amber DETECT LEDs 434d and/or provide an audible alarm. The alarm may, for example, beep a continuous solid tone as long as the transponder is detected, with a minimum of beep duration of, for instance 0.5 second.

If the software 200 detects the probe 112 is disconnected while in the Scan Mode 714, the software 200 enters the Scan Fault Mode 720. In the Scan Fault Mode 720, the software 200 may issue a sequence of rapid beeps and blink ON and OFF the amber DETECT LEDs 434d. The Scan Fault Mode 720 can be cleared by pushing the Start/Stop button. The software 200 will automatically clear the Scan Fault Mode 720 after 10 beeps.

While in the Scan Mode 714, if excess noise or loss of transmit signal is detected, the software 200 will progress to the Environment Error Mode 722. In the Environment Error Mode 722, the software 200 may issue or produce an appropriate indication. For example, the software 200 may cause the production of a sequence of slow beeps and the blinking ON and OFF the green circle LEDs 434e. The corrective action for the Environment Error Mode 722 is to reposition the probe 112 away from large metal objects or sources of electrical interference. The software 200 will automatically stop the scan if the environment error condition lasts for more than a set time or number of beeps (e.g., 5 beeps).

FIG. 8 shows a method 800 of operating an interrogation and detection system, according to one illustrated embodiment. The method 800 may be implemented by any of the interrogation and detection system embodiments discussed above.

During each of a plurality of detection cycles, the interrogation and detection system performs a number of acts 802-814. At 802, the interrogation and detection system receives electromagnetic signals, for example unmodulated electromagnetic signals, during a noise detection portion of the detection cycle. The below descriptions will be presented in terms of unmodulated electromagnetic signals due to the unique technical advantages realized by a system that employs simple resonant transponders without any on-board memory or storage, and from which information cannot be read from or written to. However, some embodiments may employ readable and/or writable transponders, for instance radio frequency identification (RFID) transponders or tags, which respond with a modulated electromagnetic signal that encodes information in the modulation. The various techniques described herein are applicable to such transponders and modulated electromagnetic signals.

At 804, the interrogation and detection system determines a noise value indicative of a noise level that corresponds to a highest one of a number N of samples or measurements of the unmodulated electromagnetic signals received during the noise detection portion of the detection cycle, where the number N is greater than one. At 806, the interrogation and detection system adjusts a signal detection threshold based at least in part on the determined noise value of at least one of the detection cycles.

At 808, the interrogation and detection system emits at least one electromagnetic interrogation signal during a transmit portion of the detection cycle. At 810, the interrogation and detection system receives unmodulated electromagnetic signals during a receive response portion of the detection cycle that follows the transmit portion of the detection cycle.

At 812, the interrogation and detection system determines the presence or absence of a transponder based at least in part on a number M of samples or measurements of the unmodulated electromagnetic signals received during the detection cycle and the adjusted signal detection threshold, where the number M is greater than one. A ratio of N:M may be at least equal to 4. N may be equal to about 200 and M may be equal to about 800.

The interrogation and detection system may determine a noise value indicative of a noise level based at least in part on the unmodulated electromagnetic signals received during the noise detection portion of the detection cycle by setting the noise value based on the highest one of six samples or measurements of the unmodulated electromagnetic signal received during the noise detection portion of the detection cycle.

The interrogation and detection system may adjust the signal detection threshold by adjusting the signal detection threshold based at least in part on a first number of determined noise values indicative of a noise level during at least one noise detection portion that occurred before the receive response portion of a first one of the detection cycles and a second number of determined noise values indicative of a noise level during at least one noise detection portion that occurred after the receive response portion of the first one of the detection cycles.

The interrogation and detection system may adjust the signal detection threshold based at least in part on the determined noise value of at least one of the detection cycles by adjusting the signal detection threshold to be approximately twice an average of at least one of the first and the second number of determined noise values.

The interrogation and detection system may adjust the signal detection threshold based at least in part on the determined noise value of at least one of the detection cycles by adjusting the signal detection threshold to be approximately twice a greatest one of at least one of the first and the second number of determined noise values.

The interrogation and detection system may determine the presence or absence of a transponder by comparing a maximum value of a plurality of matched filter outputs with the adjusted signal threshold.

The interrogation and detection system may adjust the signal detection threshold based at least in part on the determined noise value of at least one of the detection cycles by adjusting the signal detection threshold to be approximately twice the determined noise value.

The interrogation and detection system may adjust the signal detection threshold based at least in part on the determined noise value of at least one of the detection cycles includes adjusting the signal detection threshold to be the large of approximately twice the determined noise value or a defined threshold value. The defined threshold value may for example be approximately 0.5 mV.

In some embodiments, the interrogation and detection system determines if an output of at least one matched filter during the noise detection portion of the detection cycle exceeds a noise fault threshold indicative of a noise fault.

In some embodiments, the interrogation and detection system determines if the output of the at least one matched filter during the noise detection portion of the detection cycle exceeds the noise fault threshold for a defined period of time. The interrogation and detection system may terminates the detection cycle in response to the output of the at least one matched filter exceeding the noise fault threshold for the defined period of time.

The interrogation and detection system may convert the received signal(s) from the time domain to the frequency domain spectrum. The interrogation and detection system may, for example, perform a Fourier transform, for instance a fast Fourier transform such as a 256 point fast Fourier transform. Suitable algorithms and/or sets of software code for performing such are available or can be written.

The interrogation and detection system may search the frequency domain spectrum to determine the object with the strongest resonance in a defined frequency band. For example, the interrogation and detection system may search the frequency domain spectrum from about 120 kHz to about 175 kHz. An amplitude of the resonant object may be computed as the sum of the resonant power plus and minus 2 fast Fourier transform bins from the peak resonance frequency. This approach may provide a more accurate measurement of power than simply using the peak value. The frequency of the resonant object may be computed using an interpolation approach. This approach may provide a more accurate determination of resonant frequency than simply using the fast Fourier bin number.

The interrogation and detection system may determine the presence or absence of a transponder based at least in part on a frequency of the unmodulated electromagnetic signals received during the detection cycle being within a defined frequency range. The defined frequency range may extend from about 137 kHz to about 160 kHz.

The interrogation and detection system may determine a Q value (i.e., Quality factor) of the resonant object from a signal decay slope for the received unmodulated electromagnetic signal(s) returned by the resonant object. The interrogation and detection system may, for example, use multiple windows, for instance five (5) window positions may provide suitable results.

The interrogation and detection system may determine the presence or absence of a transponder based at least in part on a Q value of the unmodulated electromagnetic signal(s) received during the detection cycle. The interrogation and detection system may preferably employ the Q value determination in conjunction with determination based on the frequency and on the determination based on the adjusted signal detection threshold.

In some embodiments, the interrogation and detection system determines the presence or absence of a transponder is based at least in part on a Q value of the unmodulated electromagnetic signals received during the detection cycle being at least equal to a threshold Q value. The threshold Q value may be 35, for example. The interrogation and detection system may preferably employ the Q value determination in conjunction with determination based on the frequency and on the determination based on the adjusted signal detection threshold.

Consequently, tag detection may advantageously be based on the received unmodulated electromagnetic signal(s) satisfying all three conditions: 1) measured amplitude is above a threshold, which may be an adjustable threshold, 2) measured frequency is between a lower limit and an upper limit, and 3) measured Q value is above a minimum Q threshold. Interference, for example from RFID tags or EKG cables, are rejected when any of the following three conditions are satisfied: a) measured frequency is below the lower frequency limit, b) measured frequency is above the upper frequency limit, or c) measured Q value is below the threshold Q value. Such may provide significantly superior results over previous approaches, preventing false positives which could otherwise cause a patient to remain open for longer period of time during surgery and tie up hospital personnel and resources.

FIG. 9 shows a graph 900 of a simulated transponder response signal 902 and a noise signal 904. The inexpensive transponders usable with embodiments disclosed herein typically have a relatively large variation in the frequency of signals they emit, making it difficult to accurately detect the signals returned by the transponders. This may be particularly difficult in some environments which are noisy with respect to the particular resonant frequencies of the transponders. For example, operating rooms may have one or more electronic medical devices that emit RF noise that is harmonically synchronous with the response signals received from the transponders. Consequently, even though the responses signals may be received synchronously with the transmitted interrogation signals, noise that is harmonically synchronous with the response signals may still be high if the peaks of the noise occur at times the interrogation and detection system is expecting to see response signals from a transponder.

The transponder response signal 902 may, for example, be a nominal periodic signal centered around a particular frequency (e.g., 136 kHz, 145 kHz, 154 kHz, etc.). The noise signal 904 may be emitted from an electronic medical device located proximate to the interrogation and detection system 104 (FIG. 1), for example. In this illustration, the amplitude of the noise signal 904 is much greater than the amplitude of the transponder response signal 902. As shown, at a point 906 in time the noise signal 904 is at a peak and the transponder response signal 902 is near its zero crossing. If the interrogation and detection system 104 were to obtain a sample at the point 906 the noise signal 904 would mask the transponder response signal 902. Conversely, at points 908 and 910, the noise signal 904 is at or close to its zero crossing while the transponder response signal 902 is near its peak. If the interrogation and detection system 104 can sample the simulated response signal 902 at times when the noise signal 904 is at its zero crossing or at a low amplitude, it is possible for the interrogation and detection system to detect a transponder through the noise signal 904 (or "noise floor") that is many times greater than the transponder response signal 902. The process described below may provide a SNR of approximately five times greater than what is achieved using conventional scanning processes.

To accomplish this, in some embodiments the scanning process for each antenna 306 (FIG. 1) or coil is broken down into $N_{SS}$ subsample scan cycles for each transmit frequency. Each of the subsample scan cycles includes one or more interrogation cycles. As discussed in further detail below, each of the interrogation cycles in a particular one of the $N_{SS}$ subsample scan cycles is shifted forward in time a fraction of the period (T) of a nominal expected transponder response signal 902 (e.g., a phase shift) to provide $N_{SS}$ opportunities to avoid harmonic noise being synchronous in time with the desired transponder response signal.

FIG. 10 illustrates timing for a single interrogation cycle 1010 in an embodiment that utilizes the aforementioned subsample scan cycles, according to one illustrated embodiment. Each of the $N_{SS}$ subsample scan cycles may include one or more interrogation cycles 1010, as discussed below. The custom logic in the FPGA 508 (FIG. 5) generates the timing and control signals for each interrogation cycle 1010. During a transmit portion 1010a of the interrogation cycle 1010, the logic of the FPGA 508 drives transistor control lines to generate the transmit signal. The FPGA logic controls the frequency of the transmit signal. In some embodiments, the transmit portion 1010a has a duration of 200 microseconds (μs), for example. During a dump portion 1010b of the interrogation cycle 1010, the logic of the FPGA 508 drives a gate of a dump TRIAC to quickly drain the transmit energy from the antenna 306 to allow detection of the response signal from the transponder 116, if any. In some embodiments, the dump portion 1010b has a duration of 10 μs, for example. A recovery portion 1010c of the interrogation cycle 1010 allows receive filters and amplifiers to recover from the transmitted signal before detecting the response signal from the transponder 116, if any. The recovery portion 1010c may have a duration of 100 μs, for example. During a receive response portion 1010d of the interrogation cycle 1010, the FPGA 508 controls the signal ADC 128 to sample the response signal from the transponder 116, if any. The signal ADC 128 may, for example, sample at a 1 MHz sample rate (i.e., 1 sample per μs) with a 12-bit resolution. In some embodiments, the receive response portion 1010d has a duration of 512 μs, such that the signal ADC 128 obtains 512 measurements at the 1 MHz sample rate during the receive response portion 1010d. A skip portion 1010e of the interrogation cycle 1010 may be provided during which time measurements from the signal ADC 128 are skipped or ignored. In some embodiments the skip portion 1010e has a duration of 40 μs. The timing of the receive response portion 1010d may be such that the transponder response signal is synchronous to the transmit time.

A subsample scan cycle delay period 1010f of the interrogation cycle 1010 has a unique duration for interrogation cycles associated with a particular one of the $N_{SS}$ subsample scan cycles. Interrogation cycles associated with different ones of the $N_{SS}$ subsample scan cycles may have subsample scan cycle delay periods 1010f having differing durations. In some embodiments, the subsample scan cycle delay period 1010f associated with respective ones of the $N_{SS}$ subsample scan cycles may be approximately a fraction of the period (T) of the expected transponder response signal 902 (FIG. 9). For example, the subsample scan cycle delay periods 1010f for interrogation cycles associated with subsample scan cycles 1 to $N_{SS}$ may be approximately:

$(0/N_{SS}) * T$ for interrogation cycles of subsample scan cycle 1;

$(1/N_{SS}) * T$ for interrogation cycles of subsample scan cycle 2;

$(2/N_{SS}) * T$ for interrogation cycles of subsample scan cycle 3;

...

$((N_{SS} - 1)/N_{SS}) * T$ for interrogation cycles of subsample scan cycle $N_{SS}$.

Thus, the period (T) of the expected transponder response signal is divided into $N_{SS}$ start times, with each of the $N_{SS}$ subsample scan cycles being associated with a different one of the start times.

FIG. 11A is a timing diagram 1100 illustrating an overall instrument scan cycle 1102, according to one illustrated embodiment. The instrument scan cycle 1102 may be implemented by the interrogation and detection system 104 to scan for one or more resonant transponders. The instrument scan cycle 1102 may have a duration between a start time and a stop time that is less than about 20 seconds (e.g., two seconds, five seconds, 10 seconds, 15 seconds, etc.) so that the user operating the interrogation and detection system 104 does not need to wait an extended period of time to perform a scan operation. The instrument scan cycle 1102 may be executed one or more times during the Scan Mode of the interrogation and detection system 104. As discussed in further detail below, each instrument scan cycle 1102 may include one or more coil scan cycles, which may include one or more frequency specific sample cycles, which may include one or more subsample scan cycles, which may include one or more interrogation cycles.

The instrument scan cycle 1102 includes a number $N_{COILS}$ of coil scan cycles 1104, one coil scan cycle for each of $N_{COILS}$ present in the interrogation and detection system 104. For example, the system 104 may include three antenna coils ($N_{COILS}=3$), mutually orthogonal to each other, such that each instrument scan cycle 1102 includes three coil scan cycles 1104. In some embodiments the system 104 may include six antenna coils ($N_{COILS}=6$), or a greater or fewer number of antenna coils. In some embodiments, the system 104 includes a single coil ($N_{COILS}=1$), such that only a single coil scan cycle 1104 is performed during each instrument scan cycle 1102.

FIG. 11B is a timing diagram 1106 illustrating a cycle for one of the coil scan cycles 1104 shown in FIG. 11A, according to one illustrated embodiment. The coil scan cycle 1104 includes a number $N_{FREQ}$ of frequency specific sample cycles 1108, one for each transmit frequency to be used by the interrogation and detection system 104. The number $N_{FREQ}$ of frequency specific sample cycles 1108 may be any suitable value, such as one, two, five, eight, etc. For example, in some embodiments the interrogation and detection system 104 may transmit interrogation signals at 139 kHz, 145 kHz, and 154 kHz during frequency specific sample cycle 1, frequency specific sample cycle 2, and frequency specific sample cycle 3, respectively. In some embodiments, the interrogation and detection system 104 may transmit at a single frequency, such that only a single frequency specific sample cycle 1108 is performed during each coil scan cycle 1104.

FIG. 11C is a timing diagram 1110 illustrating a cycle for one of the frequency specific sample cycle 1108, according to one illustrated embodiment. The frequency specific sample cycle 1108 includes a number $N_{SS}$ of subsample scan cycles 1112, one for each subsample to be collected by the interrogation and detection system 104. As used herein, a subsample may refer to measurements obtained during a subsample scan cycle. As discussed above, the number $N_{SS}$ of subsample scan cycles 1112 in each frequency specific sample cycle may be any suitable value, such as two, five, 10, 15, etc. As discussed above, each of the $N_{SS}$ subsample scan cycles has a unique subsample scan cycle delay period associated therewith. The subsample scan cycle delay periods for each of the $N_{SS}$ subsample scan cycles are applied during respective interrogation cycles associated with the respective subsample scan cycles.

FIG. 11D is a timing diagram 1114 illustrating one cycle of one of the subsample scan cycles 1112, according to one illustrated embodiment. The subsample scan cycle 1112 includes a number $N_I$ of interrogation cycles 1010 (FIG. 10).

As discussed below with reference to the example shown in FIG. 12, each of the $N_I$ interrogation cycles 1010 has a subsample scan cycle delay period 1010f associated with one of the particular subsample scan cycles 1112. In other words, interrogation cycles 1 to $N_I$ for one of the subsample scan cycles 1112 all have the same subsample scan cycle delay period 1010f. The number of interrogation cycles ($N_I$) per subsample scan cycle 1112 may be any suitable value, such as 10, 250, 500, or 1000 interrogation cycles per subsample scan cycle.

FIG. 12 illustrates a timing diagram 1200 for performing $N_{SS}$ subsample scan cycles 1202 (labeled subsample scan cycles 1-7) to obtain $N_{SS}$ subsamples, where $N_{SS}$ equals seven in this illustrated example. In this embodiment, each of the subsample scan cycles 1-7 include 250 interrogation cycles 1010 (FIG. 10). Each of the interrogation cycles is designated as $I_{X-Y}$, where X is the subsample scan cycle with which the interrogation cycle is associated and Y is the number of the interrogation cycle within the subsample scan cycle. For example, $I_{2-3}$ represents the third interrogation cycle 1010 in subsample scan cycle 2. During a particular frequency specific sample cycle 1108 (FIG. 11) of a coil scan cycle 1104, the interrogation and detection system 104 performs subsample scan cycles 1-7 using a particular antenna coil (e.g., coil 306a of FIG. 3B) by sequentially executing interrogation cycles $I_{1-1}$ to $I_{1-250}$, $I_{2-1}$ to $I_{2-250}$, $I_{3-1}$ to $I_{3-250}$, $I_{4-1}$ to $I_{4-250}$, $I_{5-1}$ to $I_{5-250}$, $I_{6-1}$ to $I_{6-250}$, and $I_{7-1}$ to $I_{7-250}$, for a total of 1750 interrogation cycles, in this embodiment. Table 2 below shows the approximate subsample scan cycle delay periods 1010f for interrogation cycles 1010 within each of the subsample scan cycles 1-7.

TABLE 2

| Subsample Scan Cycle | Subsample Scan Cycle Delay Period for Interrogation Cycles in Subsample Scan Cycle | Subsample Scan Cycle Delay Period: Response Signal at 145 kHz (T = 6.9 μs) |
|---|---|---|
| 1 | (0/7)*T | 0 μs |
| 2 | (1/7)*T | ~1 μs |
| 3 | (2/7)*T | ~2 μs |
| 4 | (3/7)*T | ~3 μs |
| 5 | (4/7)*T | ~4 μs |
| 6 | (5/7)*T | ~5 μs |
| 7 | (6/7)*T | ~6 μs |

In the illustrated embodiment, the subsample scan cycle delay periods 1010f are evenly spaced across the duration of the period (T) of the expected transponder response signal. For example, for a transponder response signal expected to have a center frequency of about 145 kHz, the period T is approximately 6.9 μs. Accordingly, interrogation cycles of a next successive subsample scan cycle has a subsample scan cycle delay period 1010f that is about 1/7 of the transponder response signal period T greater than interrogation cycles of a previous successive subsample scan cycle. As an example, the subsample scan cycle delay period 1010f for interrogation cycles $I_{4-1}$ to $I_{4-250}$ of subsample scan cycle 4 is three (3) μs and the subsample scan cycle delay period 1010f for interrogation cycles $I_{5-1}$ to $I_{5-250}$ of subsample scan cycle 5 is four (4) μs. By utilizing seven different subsample scan cycle delay periods 1010f spread across the duration of the period T of the expected transponder response signal, the probability of a sampling at a time of low harmonically synchronous noise and high transponder response signal is increased. In some embodiments, more or less than seven subsample scan cycles may be used.

In some embodiments, the subsample scan cycle delay periods 1010f of the interrogation cycles may be different fractions of the period (T) of the expected transponder response signal, offset by one or more periods T. For example, in some embodiments with four subsample scan cycles, interrogation cycles of a subsample scan cycle 1 may have a subsample scan cycle delay period of T (i.e., (0/4)*T+T), such that the subsample scan cycle delay period is offset by one period T relative to the example provided in Table 2. Similarly, interrogation cycles of a subsample scan cycle 2 may have a subsample scan cycle delay period of (5/4)*T (i.e., (1/4)*T+T=(5/4)*T), interrogation cycles of a subsample scan cycle 3 may have a subsample scan cycle delay period of (6/4)*T (i.e., (2/4)*T+T=(6/4)*T), and interrogation cycles of a subsample scan cycle 4 may have a subsample scan cycle delay period of (7/4)*T (i.e., (3/4)*T+T=(7/4)*T). Importantly, the subsample scan cycle delay periods for the interrogation cycles in respective subsample scan cycles are different fractions of the expected transponder response signal. Other values for the subsample scan cycle delay periods may be used to obtain samples at different start times within the period T of the expected transponder response signal.

FIG. 13 shows a method 1300 of operating an interrogation and detection system to implement a coil scan cycle 1104 (FIGS. 11A-D), according to one illustrated embodiment. The method 1300 may be implemented by any of the interrogation and detection system embodiments discussed above. The method 1300 may be used to collect subsamples using the subsample scan cycles including the interrogation cycles 1010 illustrated in FIGS. 10 and 12 for a single antenna coil. The method 1300 may be repeated for interrogation and detection systems utilizing a plurality of antenna coils (e.g., three mutually orthogonal antenna coils).

The method starts at 1302. The method 1300 may, for example, start when an interrogation and detection system enters the Scan Mode 714 (FIG. 7). At 1304, the interrogation and detection system initializes a control variable FREQUENCY_COUNT that may be used for comparison with a number of frequency bands to be used in the coil scan cycle (i.e., the number of frequency specific sample cycles 1108). In some embodiments, more than one frequency band may be used during the coil scan cycle. For example, a first interrogation signal may be centered around 139 kHz, a second interrogation signal may be centered around 145 kHz, and a third interrogation signal may be centered around 154 kHz, for a total of three frequency specific sample cycles. Other center channels or frequencies may for example be 136 kHz, 142 kHz, 148 kHz, and or 151 kHz, or any other frequency suitable for exciting the transponder to resonate.

At 1306, the interrogation and detection system initializes a control variable SUBSAMPLE_COUNT. This control variable may be used during the method 1300 for comparison with a number of subsample scan cycles $N_{SS}$ to be executed by the interrogation and detection system. In the example shown in FIG. 12, the number of subsample scan cycles $N_{SS}$ is seven, but more or less subsample scan cycles may be used depending on how many divisions or start times in the period T of the expected transponder response signal are to be used. If $N_{SS}$ is relatively small, the probability of sampling at a time of low harmonically synchronous noise is reduced since the number of opportunities is reduced. If $N_{SS}$ is relatively large, the probability of sampling at a time of low harmonically synchronous noise is increased, but a tradeoff is that the total time for the coil scan cycle 1104 may also be increased.

At 1308, the interrogation and detection system initializes a control variable INTERROGATION_COUNT. This control variable may be used during the method 1300 for comparison with the number $N_I$ of interrogation cycles 1010 in each subsample scan cycle. In the example of FIG. 12, each subsample scan cycle includes 250 interrogation cycles 1010. More or less interrogation cycles per subsample scan cycle may be used.

At 1310, the interrogation and detection system begins a first interrogation cycle (interrogation cycle 1) for a first subsample scan cycle (subsample scan cycle 1) by emitting an electromagnetic interrogation signal centered at first frequency (frequency specific sample cycle 1) during a transmit portion 1010a of the interrogation cycle (see FIGS. 10 and 11). At 1312, the interrogation and detection system receives unmodulated electromagnetic signals during a receive response portion 1010d of the interrogation cycle that follows the transmit portion 1010a of the interrogation cycle. As discussed above with reference to FIG. 10, the interrogation cycle may include a dump portion 1010b, recovery portion 1010c, and/or a skip portion 1010e between the transmit portion 1010a and the receive response portion 1010d. The timing of the receive response portion 1010d may be such that the expected transponder response signal is synchronous or coherent with the transmit portion 1010a to improve the likelihood that peaks of the transponder response signal are detected. During the receive response portion 1010d of the interrogation cycle, the FPGA 508 controls the signal ADC 128 to sample the response signal from the transponder. The signal ADC 128 may, for example, obtain 512 measurements in 512 μs by sampling at a 1 MHz sample rate (i.e., 1 sample per μs). In some embodiments the signal ADC 128 may sample at different rates and may obtain more or less measurements during each receive response portion 1010d.

At 1314, the interrogation and detection system waits a subsample scan cycle delay period 1010f, which in some embodiments is a fraction of the period T of the expected transponder response signal, before starting the next interrogation cycle at 1310. The subsample scan cycle delay period may be approximately equal to ((SUBSAMPLE_COUNT−1)/$N_{SS}$) times the period (T) of the expected transponder response signal, in some embodiments. Thus, for interrogation cycles associated with subsample scan cycle 1, the subsample scan cycle delay period is approximately zero seconds (i.e., (0/$N_{SS}$)*T=0). For interrogation cycles associated with subsample scan cycle 2, the subsample scan cycle delay period is approximately equal to (1/$N_{SS}$)*T, and so on as discussed above.

At 1316, the interrogation and detection system increments the control variable INTERROGATION_COUNT. At 1318, the interrogation and detection system compares the value of INTERROGATION_COUNT to the number of interrogation cycles $N_I$ per subsample scan cycle. The interrogation and detection system thus continues to loop through acts 1310-1314 (i.e., interrogation cycles) until all of the interrogation cycles in subsample scan cycle 1 have been executed. The number of interrogation cycles per subsample scan cycle may be any suitable value, such as 1, 100, 250, 500, 2000, etc.

Once all of the interrogation cycles for subsample scan cycle 1 have been executed (i.e., decision 1318=YES), the interrogation and detection system increments the control variable SUBSAMPLE_COUNT at 1320, and compares its value to the number of subsample scan cycles $N_{SS}$ at 1322. Thus, similar to the acts for subsample scan cycle 1, the interrogation and detection system executes the acts 1310-1314 for subsample scan cycle 2 to subsample scan cycle $N_{SS}$ to complete a total of $N_{SS}$ subsample scan cycles and collect $N_{SS}$ subsamples.

Once all of the interrogation cycles for each of the subsample scan cycles 1 to $N_{SS}$ have been executed (i.e., decision 1322=YES), the interrogation and detection system increments the control variable FREQUENCY_COUNT at 1324 and compares its value to the number of transmit frequencies ($N_{FREQ}$) at 1326. If the number of transmit frequencies $N_{FREQ}$ is greater than one, the interrogation and detection system repeats the acts discussed above to perform $N_{SS}$ subsample scan cycles at each of the number $N_{FREQ}$ of transmit frequencies for a total of $N_{FREQ}$ frequency specific sample cycles.

The method 1300 may terminate at 1328 until started again. As discussed above, the method 1300 may repeat for one or more additional antenna coils of the interrogation and detection system. The method 1300 may continually repeat when the interrogation and detection system is in the Scan Mode. Alternatively or additionally, the method 1300 may run concurrently with other methods or processes.

FIG. 14 shows a method 1400 of operating an interrogation and detection system to execute an instrument scan cycle 1102 (FIG. 11), according to one illustrated embodiment. The method 1400 may be implemented by any of the interrogation and detection system embodiments discussed above. The method 1400 may be used to collect subsamples by performing subsample scan cycles using the interrogation cycles illustrated in FIGS. 10 and 12.

The method starts at 1402. The method 1400 may, for example, start when an interrogation and detection system enters the Scan Mode 714 (FIG. 7). At 1404, the interrogation and detection system initializes a control variable COIL_COUNT. This control variable may be used during the method 1400 for comparison with a number of coils ($N_{COILS}$) included in the interrogation and detection system. For example, in some embodiments the interrogation and detection system may include a plurality of coils or antennas that may be used to scan for transponders. In some embodiments, the interrogation and detection system may include a plurality of coils spaced apart from each other that are each designed to detect transponders in different physical locations. For example, in some embodiments six coils may be spaced apart in or on a mat positioned under a patient on a patient support structure. The six coils may be used to detect transponders at different locations proximate to the patient's body. In some embodiments, multiple coils may be provided to transmit or receive signals in multiple directions (e.g., x-, y-, and z-directions).

At 1406, the interrogation and detection system performs a coil scan cycle 1104 (FIG. 11A) to detect transponders using a first coil. The interrogation and detection system may execute this act using the method 1300 of FIG. 13 discussed above to perform a coil scan cycle 1104, which may include $N_{FREQ}$ frequency specific sample cycles, each of which may include $N_{SS}$ subsample scan cycles, each of which may include $N_I$ interrogation cycles. At 1408, the interrogation and detection system increments the control variable COIL_COUNT and compares its value to the number of coils at 1410. If the interrogation and detection subsystem includes additional coils, the system sequentially performs coil scan cycles 1104 in round robin fashion for each of the coils to scan for transponders.

The method 1400 may terminate at 1412 until started again. The method 1400 may continually repeat when the interrogation and detection system is in the Scan Mode.

Alternatively or additionally, the method 1400 may run concurrently with other methods or processes.

FIG. 15 shows a method 1500 of operating an interrogation and detection system, according to one illustrated embodiment.

At 1502, the interrogation and detection system determines the presence or absence of a transponder based at least in part on at least one of the subsamples obtained by performing the method 1300 and/or the method 1400 discussed above (FIGS. 13 and 14).

As discussed above, the signal ADC 128 (FIG. 5) converts the signal received from the transponder, if any, from analog to digital. Such conversion may, for example, be performed at a sampling rate of 1 MHz with a 12-bit data resolution. In the example shown in FIG. 12, subsample scan cycles 1-7 each include 250 interrogation cycles, and the signal ADC 128 obtains 512 measurements per interrogation cycle. The sampled ADC data for each subsample scan cycle may be accumulated together or integrated to compute the total summed response signal received from the transponder 116, if any, for each subsample.

In some embodiments, the accumulated or integrated received signal for each subsample is matched filtered with both in-phase and quadrature reference signals to determine the signal magnitude. The received response signal may be matched filtered with a plurality of reference signals, for example with the seven reference signals, for instance as shown in Table 1 above. Some embodiments may employ matched filtering before accumulating or integrating the received signal.

For each subsample collected, the maximum value for the matched filters (e.g., seven matched filters) with active transmit may be compared with an adjusted detection threshold. If the maximum value is greater than the detection threshold for one or more subsamples, then a response signal from a transponder is considered as having been detected, and appropriate action is taken, such as discussed above with reference to FIG. 7. In some embodiments, a value greater than the detection threshold for two or more subsamples is required before a transponder is considered to have been detected.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other transponders and interrogation and detection systems, not necessarily the exemplary surgical object transponders and interrogation and detection systems generally described above.

For instance, the foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms of taught herein are capable of being distributed as a program product in a variety of forms, and that an illustrative embodiment applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory; and transmission type media such as digital and analog communication links using TDM or IP based communication links (e.g., packet links).

The various embodiments described above can be combined to provide further embodiments. U.S. Provisional Patent Application Ser. No. 61/056,787, filed May 28, 2008; U.S. Provisional Patent Application Ser. No. 61/091,667, filed Aug. 25, 2008; U.S. Provisional Patent Application No. 60/811,376 filed Jun. 6, 2006; U.S. Pat. No. 6,026,818, issued Feb. 22, 2000; U.S. Patent Publication No. US 2004/0250819, published Dec. 16, 2004; U.S. provisional patent application Ser. No. 60/811,376, filed Jun. 6, 2006, U.S. non-provisional patent application Ser. No. 11/743,104, filed May 1, 2007 and U.S. provisional patent application Ser. No. 61/972,832, filed Mar. 31, 2014, are incorporated herein by reference, in their entirety. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of operating a transponder detection device that includes at least one processor, at least one nontransitory processor-readable medium communicatively coupled to the at least one processor and which stores at least one of instructions or data executable by the at least one processor, the method comprising:

during each of a number of successive interrogation cycles, the number of successive interrogation cycles being greater than one,
emitting a periodic electromagnetic interrogation signal during a transmit portion of the interrogation cycle;
receiving electromagnetic signals during a receive response portion of the interrogation cycle that follows the transmit portion of the interrogation cycle; and
waiting a respective delay period before a respective start of each of the successive interrogation cycles of the number of interrogation cycles, each respective delay period for the number of interrogation cycles equal to a respective fraction of a nominal tag response signal period, and, for each one of the successive interrogation cycles of the number of interrogation cycles, the respective delay period of the one of the successive interrogation cycles being less than a respective delay period of an immediately subsequent interrogation cycle of the number of successive interrogation cycles by a duration equal to the nominal tag response signal period divided by the number of successive interrogation cycles.

2. A method of operating a transponder detection device that includes at least one processor, at least one nontransitory processor-readable medium communicatively coupled to the at least one processor and which stores at least one of instructions or data executable by the at least one processor, the method comprising:
obtaining a number of subsamples, each of the subsamples associated with a respective delay period equal to a respective fraction of a nominal tag response signal period, the respective fractions different from one another, each of the number of subsamples obtained by:
during each of a plurality of successive interrogation cycles associated with each of the number of subsamples,
emitting a periodic electromagnetic interrogation signal during a transmit portion of the interrogation cycle;
receiving electromagnetic signals during a receive response portion of the interrogation cycle that follows the transmit portion of the interrogation cycle; and
waiting the delay period of the one of the number of subsamples to which the interrogation cycle is associated before a start of each of the successive interrogation cycles of the plurality of interrogation cycles, wherein waiting a delay period before a start of each of the successive interrogation cycles of the plurality of interrogation cycles comprises waiting a delay period before a start of each of the successive interrogation cycles of the plurality of interrogation cycles and, for each successive pair of subsamples, the delay period associated with a first successive one of the pairs of subsamples is less than the delay period associated with a next successive one of the pairs of subsamples by a duration approximately equal to the nominal tag response signal period divided by the number of subsamples.

3. The method of claim 2 wherein waiting a delay period before a start of each of the successive interrogation cycles of the plurality of interrogation cycles comprises waiting a delay period before a start of each of the successive interrogation cycles of the plurality of interrogation cycles, the delay period for each of the number of subsamples between zero seconds and the nominal tag response signal period.

4. The method of claim 2 wherein waiting a delay period before a start of each of the successive interrogation cycles of the plurality of interrogation cycles comprises waiting a delay period before a start of each of the successive interrogation cycles of the plurality of interrogation cycles, the delay period for at least one of the number of subsamples being a duration between the nominal tag response signal period and twice the nominal tag response signal period.

5. The method of claim 2 wherein waiting a delay period before a start of each of the successive interrogation cycles of the plurality of interrogation cycles comprises waiting a delay period before a start of each of the successive interrogation cycles of the plurality of interrogation cycles and, for each successive pair of subsamples, the delay period associated with a first successive one of the pairs of subsamples is less than the delay period associated with a next successive one of the pairs of subsamples.

6. The method of claim 2 wherein waiting a delay period before a start of each of the successive interrogation cycles of the plurality of interrogation cycles comprises waiting a delay period before a start of each of the successive interrogation cycles of the plurality of interrogation cycles, and the delay period associated with each subsample differs from the delay period for the other subsamples by less than the nominal tag response signal period.

7. The method of claim 2 wherein waiting a delay period before a start of each of the successive interrogation cycles of the plurality of interrogation cycles comprises waiting a delay period before a start of each of the successive interrogation cycles of the plurality of interrogation cycles, and the delay period associated with each subsample is approximately an integer multiple of the nominal tag response signal period divided by the number of subsamples.

8. The method of claim 2, further comprising:
during each of the plurality of interrogation cycles, before the receive response portion of the interrogation cycle, waiting a fixed recovery time after the transmit portion of the interrogation cycle, the fixed recovery time having a duration determined to provide synchronization between the transmit portion and the receive response portion of each interrogation cycle.

9. The method of claim 2 wherein the transponder detection device includes a plurality of antennas, the method further comprising:
obtaining a number of subsamples for each of the plurality of antennas.

10. The method of claim 2, further comprising:
determining the presence or absence of a transponder based at least in part on a number of measurements of the electromagnetic signals received during the plurality of interrogation cycles of at least one of the number of subsamples.

11. A method of operating a transponder detection device that includes at least one processor, at least one nontransitory processor-readable medium communicatively coupled to the at least one processor and which stores at least one of instructions or data executable by the at least one processor, and one or more antennas, the method comprising:
for each of the one or more antennas,
obtaining a set of subsamples, the set of subsamples comprising a number of subsamples, each of the subsamples associated with a respective delay period equal to a respective fraction of a nominal tag response signal period, the respective fractions different from one another, each of the subsamples in the set of subsamples obtained by:
during each of a plurality of successive interrogation cycles associated with each subsample in the set of subsamples,
emitting a periodic electromagnetic interrogation signal during a transmit portion of the interrogation cycle, the electromagnetic interrogation signal having an interrogation signal frequency;
receiving electromagnetic signals during a receive response portion of the interrogation cycle that follows the transmit portion of the interrogation cycle; and
waiting the respective delay period of the one of the number of subsamples in the set of subsamples to which the interrogation cycle is associated before a start of each of the successive interrogation cycles of the plurality of interrogation cycles, wherein, for each successive pair of subsamples in the set of subsamples, the delay period associated with a successive one of the pairs of subsamples is less than the delay period associated with an immediately next successive one of the pairs of subsamples by a duration equal to the nominal tag response signal period divided by the number of subsamples.

\* \* \* \* \*